(12) United States Patent
Reimer et al.

(10) Patent No.: US 12,226,314 B2
(45) Date of Patent: Feb. 18, 2025

(54) ACTIVE ALIGNMENT OF COMMISSURES IN PROSTHETIC HEART VALVE IMPLANTATION

(71) Applicant: St. Jude Medical, Cardiology Division, Inc., St. Paul, MN (US)

(72) Inventors: Jay Reimer, Saint Paul, MN (US); Peter J. Ness, Minneapolis, MN (US); Ryan Finn, St. Paul, MN (US); Daniel J. Klima, Andover, MN (US); Brandon Moore, St. Louis Park, MN (US)

(73) Assignee: ST. JUDE MEDICAL, CARDIOLOGY DIVISION, INC., St. Paul, MN (US)

( * ) Notice: Subject to any disclaimer, the term of this patent is extended or adjusted under 35 U.S.C. 154(b) by 679 days.

(21) Appl. No.: 17/450,180

(22) Filed: Oct. 7, 2021

(65) Prior Publication Data

US 2022/0125585 A1   Apr. 28, 2022

Related U.S. Application Data

(60) Provisional application No. 63/105,387, filed on Oct. 26, 2020.

(51) Int. Cl.
*A61F 2/24* (2006.01)
*A61M 25/01* (2006.01)
*A61M 25/09* (2006.01)

(52) U.S. Cl.
CPC ..... *A61F 2/2436* (2013.01); *A61M 2025/015* (2013.01); *A61M 2025/09175* (2013.01)

(58) Field of Classification Search
CPC ........... A61F 2/2436; A61M 2025/015; A61M 2025/09175
See application file for complete search history.

(56) References Cited

U.S. PATENT DOCUMENTS 3,205,863 A   9/1965 Kent
7,399,315 B2   7/2008 Iobbi
(Continued)

FOREIGN PATENT DOCUMENTS

WO   2020/051591 A1   3/2020

OTHER PUBLICATIONS

Extended European Search Report issued in Appln. No. 21204508.2 mailed Mar. 25, 2022 (8 pages).

*Primary Examiner* — Paul B Prebilic
(74) *Attorney, Agent, or Firm* — SLEMAN & LUND LLP

(57) ABSTRACT

A delivery device for a collapsible prosthetic heart valve includes an inner shaft, an outer shaft, and a distal sheath. The distal sheath may be disposed distal to the outer shaft and about a portion of the inner shaft to form a compartment with the inner shaft, the compartment being sized to receive the prosthetic heart valve in a collapsed condition. The inner shaft and the distal sheath may be movable relative to one another. The delivery device may also include a tube member and an outer sleeve overlying the tube member. The tube member may be configured to rotate or twist upon axial movement of the outer sleeve with respect to the tube member, the rotation or twisting of the tube member configured to rotate the prosthetic heart valve when the prosthetic heart valve is received within the compartment in the collapsed condition.

8 Claims, 11 Drawing Sheets

(56) References Cited

U.S. PATENT DOCUMENTS

| | | |
|---|---|---|
| 8,052,750 B2 | 11/2011 | Tuval et al. |
| 8,512,398 B2 | 8/2013 | Alkhatib |
| 9,532,868 B2 | 1/2017 | Braido |
| 9,545,306 B2 | 1/2017 | Tabor |
| 2005/0288777 A1 | 12/2005 | Rhee et al. |
| 2016/0296324 A1 | 10/2016 | Bapat et al. |
| 2016/0302920 A1* | 10/2016 | Al-Jilaihawi ......... A61F 2/2433 |
| 2018/0153693 A1 | 6/2018 | Copeland et al. |
| 2018/0153694 A1 | 6/2018 | Wilson et al. |
| 2018/0325669 A1 | 11/2018 | Morrissey et al. |
| 2019/0374342 A1 | 12/2019 | Gregg et al. |
| 2020/0016370 A1* | 1/2020 | Sasaki ................. A61M 25/005 |
| 2021/0068956 A1 | 3/2021 | Gale et al. |
| 2021/0169645 A1 | 6/2021 | Dale et al. |
| 2022/0142777 A1* | 5/2022 | Scheinblum .......... A61F 2/2418 |

\* cited by examiner

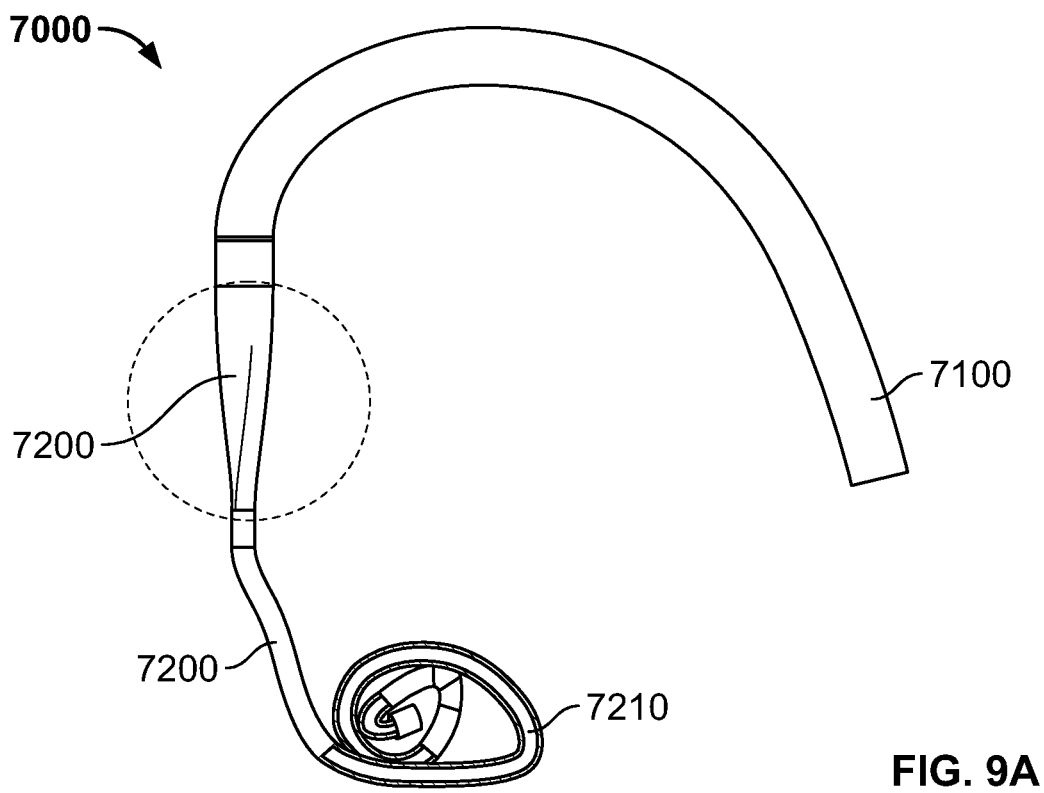
FIG. 9A
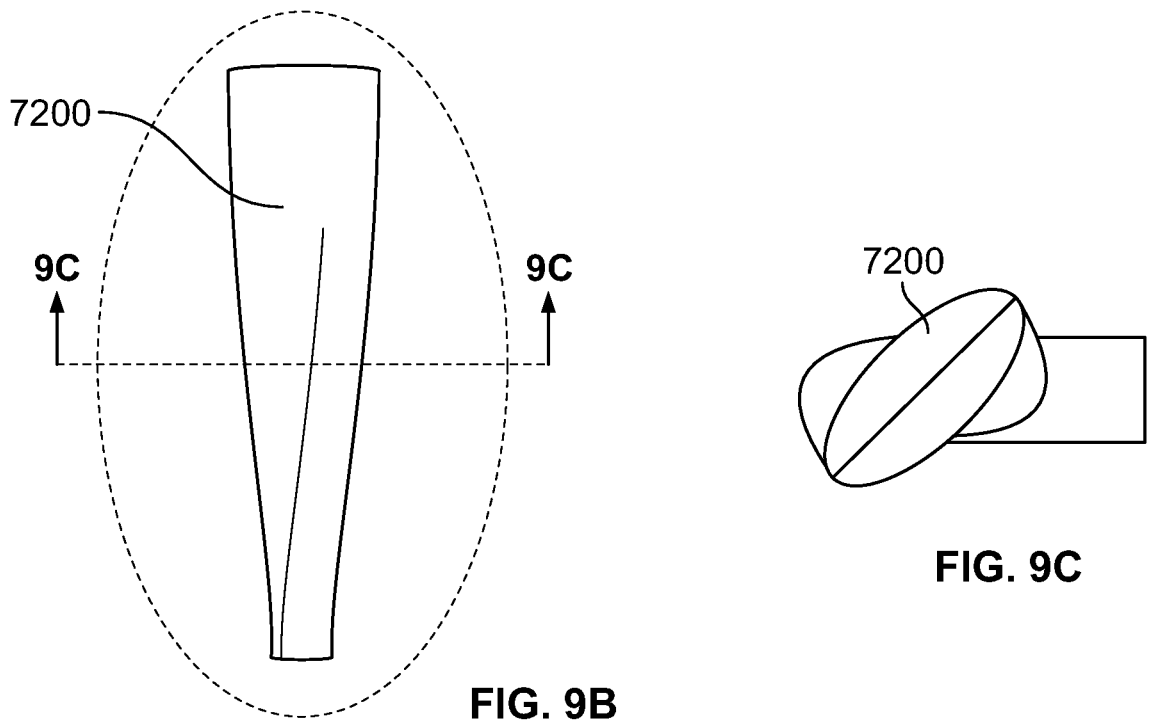
FIG. 9B
FIG. 9C

ACTIVE ALIGNMENT OF COMMISSURES IN PROSTHETIC HEART VALVE IMPLANTATION

CROSS-REFERENCE TO RELATED APPLICATIONS

This application claims the benefit of the filing date of U.S. Provisional Patent Application No. 63/105,387, filed Oct. 26, 2020, the disclosure of which is hereby incorporated by reference herein.

BACKGROUND OF THE DISCLOSURE

The present disclosure relates to systems and methods for aligning commissures of prosthetic heart valves with native commissures of the heart valve being replaced by the prosthetic heart valve.

Prosthetic heart valves that are collapsible to a relatively small circumferential size can be delivered into a patient less invasively than valves that are not collapsible. For example, a collapsible valve may be delivered into a patient via a tube-like delivery apparatus such as a catheter, a trocar, a laparoscopic instrument, or the like. This collapsibility can avoid the need for a more invasive procedure such as full open-chest, open-heart surgery.

Collapsible prosthetic heart valves typically take the form of a valve structure mounted on a stent. There are two types of stents on which the valve structures are ordinarily mounted: a self-expanding stent and a balloon-expandable stent. To place such valves into a delivery apparatus and ultimately into a patient, the valve must first be collapsed or crimped to reduce its circumferential size.

When a collapsed prosthetic valve has reached the desired implant site in the patient (e.g., at or near the annulus of the patient's heart valve that is to be replaced by the prosthetic valve), the prosthetic valve can be deployed or released from the delivery apparatus and re-expanded to full operating size. For balloon-expandable valves, this generally involves releasing the entire valve, assuring its proper location, and then expanding a balloon positioned within the valve stent. For self-expanding valves, on the other hand, the stent automatically expands as the sheath covering the valve is withdrawn.

When a prosthetic heart valve is implanted into a native heart valve, it may be desirable for the commissures of the prosthetic heart valve (e.g. the areas at which a side of one prosthetic heart valve leaflet meet with a side of an adjacent prosthetic heart valve leaflet) to rotationally align with the native commissures of the native heart valve. Such alignment may help reduce the risk of coronary obstruction, and it may be generally desirable for the prosthetic valve to mimic the native valve anatomy as closely as possible. When implanting prosthetic heart valves surgically (i.e. through an open heart, open chest procedure), there is typically good visualization of the operative field, which makes alignment of the prosthetic commissures with the native commissures relatively easy. However, in transcatheter procedures, the entire surgical field is not capable of visualization by the naked eye of the surgeon. For example, deployment of the prosthetic heart valve in a transcatheter procedure is frequently performed under fluoroscopic imaging. Also, the prosthetic heart valve is typically positioned at one end of a delivery device whereas the surgeon is manipulating the opposite end of the delivery device. This can make it significantly more difficult to align the commissures of the prosthetic heart valve with the native valve commissures during a transcatheter heart valve replacement procedure compared to a surgical heart valve replacement procedure. Thus, it would be desirable for systems and methods to help assist with aligning commissures of a prosthetic heart valve with native heart valve commissures, particularly for transcatheter implantation systems.

SUMMARY OF THE DISCLOSURE

According to one aspect of the disclosure, a delivery device for a collapsible prosthetic heart valve includes an inner shaft, an outer shaft, and a distal sheath. The distal sheath may be disposed distal to the outer shaft and about a portion of the inner shaft to form a compartment with the inner shaft, the compartment being sized to receive the prosthetic heart valve in a collapsed condition. The inner shaft and the distal sheath may be movable relative to one another. The delivery device may also include a tube member and an outer sleeve overlying the tube member. The tube member may be configured to rotate or twist upon axial movement of the outer sleeve with respect to the tube member, the rotation or twisting of the tube member configured to rotate the prosthetic heart valve when the prosthetic heart valve is received within the compartment in the collapsed condition.

According to another aspect of the disclosure, a delivery device for a collapsible prosthetic heart valve includes an inner shaft, an outer shaft, and a distal sheath. The distal sheath may be disposed distal to the outer shaft and about a portion of the inner shaft to form a compartment with the inner shaft, the compartment being sized to receive the prosthetic heart valve in a collapsed condition. The inner shaft and the distal sheath may be movable relative to one another. The delivery device may also include a tube member and a pull wire wrapped around the tube member, the pull wire having a first free end extending proximally toward a handle of the delivery device. The tube member may be configured to rotate or twist in a first rotational direction upon pulling of the first free end of the pull wire.

According to a further aspect of the disclosure, a prosthetic heart valve delivery system includes delivery device and a guidewire. The delivery device may have an inner shaft, an outer shaft, and a distal sheath disposed distal to the outer shaft and about a portion of the inner shaft to form a compartment with the inner shaft, the compartment being sized to receive the prosthetic heart valve in a collapsed condition. The inner shaft and the distal sheath may be movable relative to one another. The guidewire may have a proximal section, a distal anchoring section, and an annulus section between the proximal section and the distal anchoring section. The annulus section of the guidewire may have a non-circular cross-sectional shape that matches a non-circular cross-sectional shape of an interior guidewire lumen of the delivery device, the annulus section of the guidewire twisting along a length of the annulus section.

According to yet another aspect of the disclosure, a prosthetic heart valve delivery system includes a delivery device, a first guidewire, and a second guidewire. The delivery device may include an inner shaft, an outer shaft, and a distal sheath disposed distal to the outer shaft and about a portion of the inner shaft to form a compartment with the inner shaft, the compartment being sized to receive the prosthetic heart valve in a collapsed condition. The inner shaft and the distal sheath may be movable relative to one another. The first and second guidewires may have circular cross-sections. The delivery device may define a guidewire lumen configured to simultaneously receive therethrough the first and second guidewires, the delivery device having at most two different rotational orientations relative to the first and second guidewires when the first and second guidewires are received within the guidewire lumen.

BRIEF DESCRIPTION OF THE DRAWINGS

FIG. 9A is a front view of a guidewire according to an embodiment of the disclosure.

FIG. 9B is an enlarged isolated view of an annulus section of the guidewire of FIG. 9A.

FIG. 9C is a cross-section of the annulus section taken along the section line 9C-9C of FIG. 9B.

DETAILED DESCRIPTION OF THE DISCLOSURE

As used herein in connection with prosthetic heart valves, the term "inflow end" refers to the end of the heart valve through which blood first flows when implanted in an intended position and orientation, while the term "outflow end" refers to the opposite end, through which blood last flows when the prosthetic heart valve is implanted in the intended position and orientation. When used in connection with devices for delivering a prosthetic heart valve into a patient, the terms "proximal" and "distal" are to be taken as relative to the user of the delivery devices. In other words, in this context, "proximal" is to be understood as relatively close to the user of the delivery device, and "distal" is to be understood as relatively farther away from the user of the delivery device.

Figure 1:
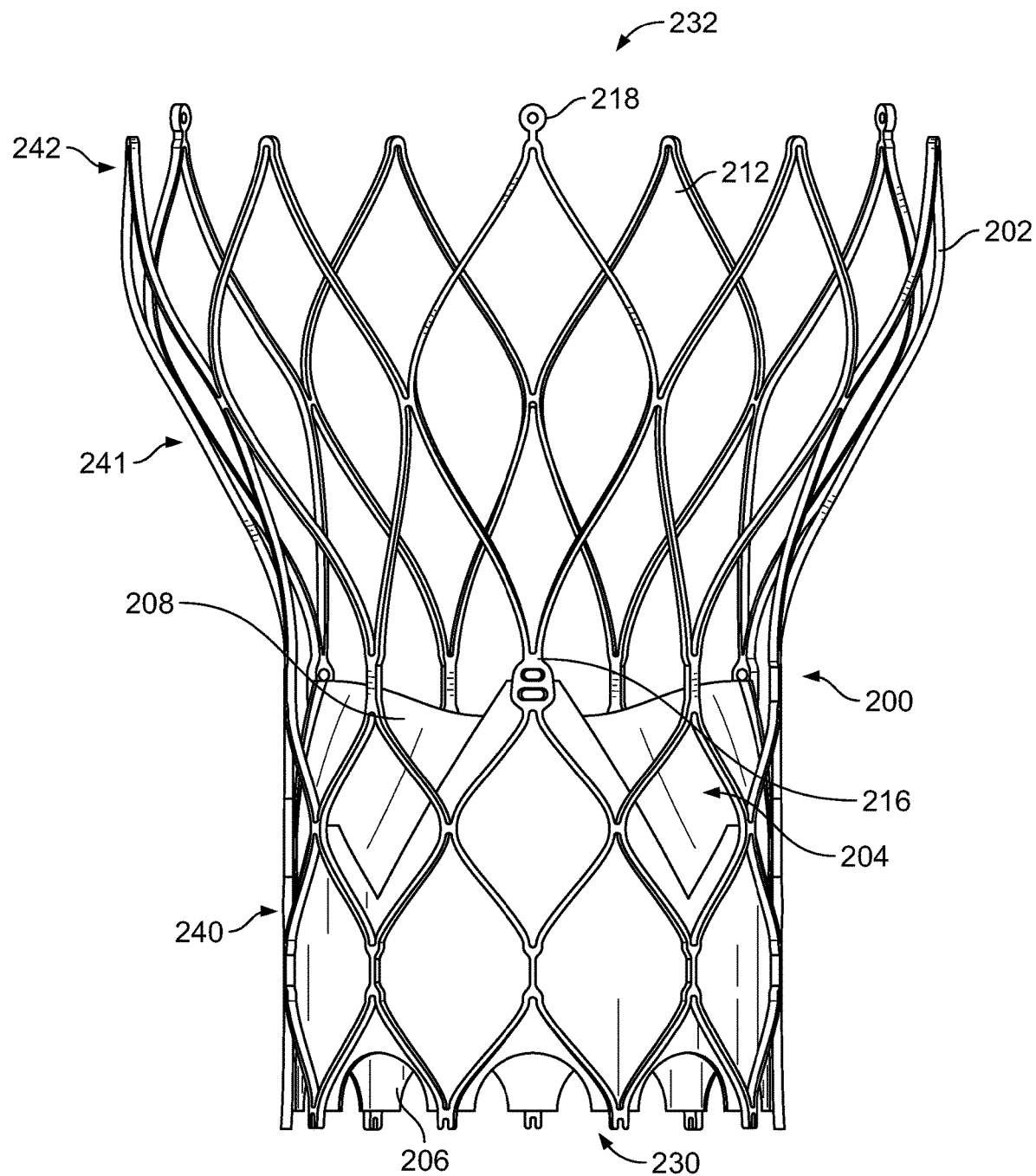
FIG. 1 is a side elevational view of a collapsible prosthetic heart valve in an expanded condition, showing the valve assembly attached to the stent.

FIG. 1 shows a collapsible prosthetic heart valve 200. The prosthetic heart valve 200 is designed to replace the function of a native aortic valve of a patient, although it should be understood that the concepts described herein may be applicable to the replacement of any native heart valve, including the mitral, tricuspid, or pulmonary heart valves. As discussed in detail below, the prosthetic heart valve has an expanded condition, shown in FIG. 1, and a collapsed condition.

Prosthetic heart valve 200 includes a collapsible and expandable stent 202 which may be formed from any biocompatible material, such as metals, metal alloys, synthetic polymers or biopolymers capable of functioning as a stent. Stent 202 extends from an inflow or annulus end 230 to an outflow or aortic end 232, and includes an annulus section 240 adjacent the inflow end and an aortic section 242 adjacent the outflow end. The annulus section 240 has a relatively small cross-section in the expanded condition, while the aortic section 242 has a relatively large cross-section in the expanded condition. Preferably, annulus section 240 is in the form of a cylinder having a substantially constant diameter along its length. A transition section 241 may taper outwardly from the annulus section 240 to the aortic section 242. Each of the sections of the stent 202 includes a plurality of cells 212 connected to one another in one or more annular rows around the stent. For example, as shown in FIG. 1, the annulus section 240 may have two annular rows of complete cells 212 and the aortic section 242 and transition section 241 may each have one or more annular rows of partial cells 212. The cells 212 in the aortic section 242 may be larger than the cells 212 in the annulus section 240. The larger cells in the aortic section 242 better enable the prosthetic valve 200 to be positioned without the stent structure interfering with blood flow to the coronary arteries.

Stent 202 may include one or more retaining elements 218 at the outflow end 232 thereof, the retaining elements being sized and shaped to cooperate with female retaining structures provided on the deployment device. The engagement of retaining elements 218 with the female retaining structures on the deployment device helps maintain prosthetic heart valve 200 in assembled relationship with the deployment device, minimizes longitudinal movement of the prosthetic heart valve relative to the deployment device during unsheathing or resheathing procedures, and helps prevent rotation of the prosthetic heart valve relative to the deployment device as the deployment device is advanced to the target location and during deployment.

The prosthetic heart valve 200 includes a valve assembly 204 positioned in the annulus section 240. Valve assembly 204 includes a cuff 206 and a plurality of leaflets 208 which collectively function as a one-way valve. The commissure between adjacent leaflets 208 may be connected to commissure features 216 on stent 202. Prosthetic heart valve 200 is shown in FIG. 1 with three leaflets 208, as well as three commissure features 216. As can be seen in FIG. 1, the commissure features 216 may lie at the intersection of four cells 212, two of the cells being adjacent one another in the same annular row, and the other two cells being in different annular rows and lying in end-to-end relationship. Preferably, commissure features 216 are positioned entirely within annulus section 240 or at the juncture of annulus section 240 and transition section 241. Commissure features 216 may include one or more eyelets which facilitate the suturing of the leaflet commissure to the stent. However, it will be appreciated that the prosthetic heart valves may have a greater or lesser number of leaflets and commissure features. For example, a prosthetic mitral valve may include two prosthetic leaflets with two commissures. Additionally, although cuff 206 is shown in FIG. 1 as being disposed on the luminal surface of annulus section 240, it is contemplated that the cuff may be disposed on the abluminal surface of annulus section 240, or may cover all or part of either or both of the luminal and abluminal surfaces of annulus section 240. Both the cuff 206 and the leaflets 208 may be wholly or partly formed of any suitable biological material or polymer.

In operation, a prosthetic heart valve, including the prosthetic heart valve described above, may be used to replace a native heart valve, such as the aortic valve, a surgical heart valve or a heart valve that has undergone a surgical procedure. The prosthetic heart valve may be delivered to the desired site (e.g., near a native aortic annulus) using any suitable delivery device, including the delivery devices described in detail below. During delivery, the prosthetic heart valve is disposed inside the delivery device in the collapsed condition. The delivery device may be introduced into a patient using a transfemoral, transapical or transseptal approach, although any transcatheter approach may suitable. Once the delivery device has reached the target site, the user may deploy the prosthetic heart valve. Upon deployment, the prosthetic heart valve expands into secure engagement within the native aortic annulus. When the prosthetic heart valve is properly positioned inside the heart, it works as a one-way valve, allowing blood to flow in one direction and preventing blood from flowing in the opposite direction.

In a prosthetic aortic heart valve, the valve assembly may be spaced from the outflow or aortic end of the stent by a distance that enables deployment of the heart valve by an amount sufficient for the valve leaflets of the prosthetic valve to operate as intended, while the outflow end of the stent remains captured by the delivery device. More particularly, the inflow or annulus end of the prosthetic heart valve may be deployed first, while the aortic or outflow end of the prosthetic heart valve remains at least partially covered by a distal sheath of the delivery device. The annulus portion of the prosthetic heart valve may be deployed so that the entirety of the valve leaflets, up to and including the commissures, is deployed and fully operational. By deploying the prosthetic heart valve in this manner, the user can determine whether the valve leaflets are properly positioned relative to the native valve annulus, and whether the valve is functioning properly. If the user determines that the positioning and operation of the valve are acceptable, the remainder of the valve may be deployed. However, if it is determined that the leaflet position is improper or that the valve is not functioning properly, the user may resheath the valve and either reposition it for redeployment, or remove it entirely from the patient.

As is shown in FIG. 1, in one embodiment the entirety of valve assembly 204, including the leaflet commissures, is positioned in the annulus section 240 of stent 202. When opened, the leaflets may extend further into the transition section 241 or may be designed such that they remain substantially completely within the annulus section. That is, substantially the entirety of valve assembly 204 is positioned between the inflow end 230 of stent 202 and the commissure features 216, and none of the valve assembly 204 is positioned between commissure features 216 and the outflow end 232 of the stent. Indeed, in some embodiments, the valve can be designed such that, upon partial deployment, the commissure features are fully exposed, oriented generally parallel to the direction of blood flow, and at or near their actual radially expanded positions (but not necessarily their eventual positions relative to the annulus), such that the leaflets can operate substantially as they would when the valve is fully deployed, even though enough of the stent is still retained within the delivery device or sheath to permit resheathing.

In one arrangement, the distance between commissure features 216 and the outflow end 232 of stent 202 will be about two-thirds of the length of the stent from the inflow end 230 to the outflow end. This structural arrangement may provide advantages in the deployment of prosthetic valve 200 as will be discussed in more detail with reference to FIGS. 2A and 2B. By having the entirety of valve assembly 204 positioned within annulus section 240, and by having a sufficient distance between commissure features 216 and the distal end 232 of stent 202, the valve assembly and commissures will not impede blood flow into the coronary arteries and will not interfere with access thereto during cardiac intervention, such as angiography, annuloplasty or stent placement.

Further, it is possible to partially deploy prosthetic valve 200 so that the valve assembly 204 thereof is able to fully function in its intended position in the native valve annulus, while a sufficient amount of the aortic section 242 is retained within the delivery device should resheathing become necessary. In other words, the user may withdraw the distal sheath of the delivery device to gradually expose prosthetic valve 200, beginning at the inflow end 230. Continued withdrawal of the distal sheath will expose a greater extent of the prosthetic valve until the entire annulus section 240 and valve assembly 204 have been exposed. Upon exposure, these portions of the prosthetic valve will expand into engagement with the native valve annulus, entrapping the native valves, except for a small portion immediately adjacent the free end of the distal sheath which will be constrained by the distal sheath from fully expanding.

However, once the distal sheath has been withdrawn to expose a sufficient portion of the aortic section 242, the annulus section 240 will be able to fully expand and valve assembly 204 will be able to function in the same manner as if the entirety of prosthetic valve 200 had been deployed. At this juncture, it will be possible for the user to ascertain whether annulus section 240 and valve assembly 204 have been properly positioned relative to the native valve annulus, and whether the valve assembly is functioning properly.

If the position and operation of valve assembly 204 are acceptable, the distal sheath may be withdrawn further to deploy the remainder of prosthetic valve 200. On the other hand, if the positioning or operation of valve assembly 204 are unacceptable, the user may advance the distal sheath to resheath the prosthetic valve, reposition the valve and initiate the deployment procedure anew. And if it is determined that the valve is not functioning properly, it can be withdrawn from the patient and a new valve introduced.

Figure 2A:
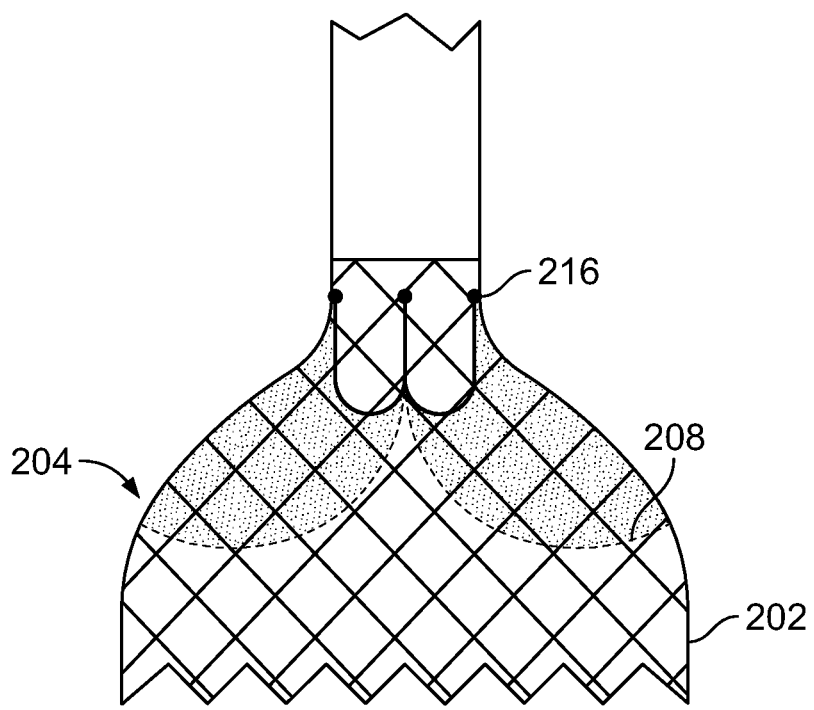
FIG. 2A is a highly schematic side elevational view showing partial deployment of a collapsible prosthetic heart valve with high placement.
Figure 2B:
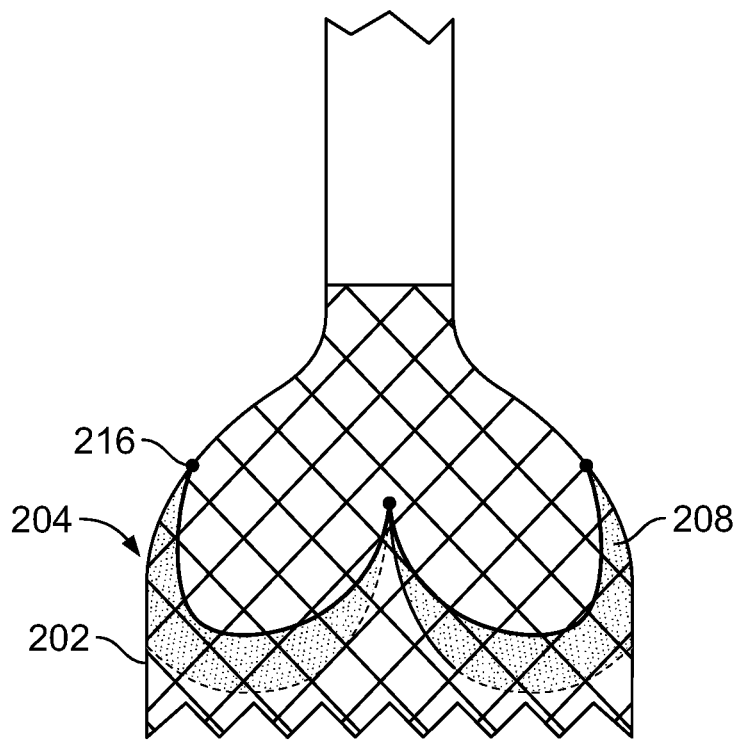
FIG. 2B is a highly schematic side elevational view showing partial deployment of a collapsible prosthetic heart valve with low placement.

It will be appreciated from the foregoing that the placement of the leaflets 208 within the stent 202 can affect the valve functioning during partial deployment. FIG. 2A illustrates a valve assembly 204 with high placement, while FIG. 2B illustrates a valve assembly with low placement. As used herein, the phrase "high placement" of a valve assembly refers to locating the valve assembly within the transition section 241 of the stent 202, or within the portion of the annulus section 240 closest to the transition section. The phrase "low placement" of a valve assembly refers to locating the valve assembly closer to the inflow end 230 of the stent 202 and entirely within the annulus section 240 thereof, such that the leaflets 208 are substantially disposed within the annulus section.

As seen in FIG. 2A, during partial deployment the annulus end of the heart valve 200 is unsheathed and allowed to expand. The outflow end 232, including the aortic section 242, remains partially sheathed and coupled to the delivery device. It should be appreciated that high placement of valve assembly 204 will cause the valve assembly to not be fully deployed when heart valve 200 is only partially deployed, thereby affecting leaflet function. Specifically, since the commissure features 216 are located closer to or within the transition section 241, they do not reach their fully expanded positions. As such, the leaflets 208 remain partially closed at this stage of deployment. Because of the location of the commissure features 216 and the leaflets 208, the valve assembly 204 cannot be tested during partial deployment. Instead, the user must unsheathe a portion of the aortic section 242 as well, which may pose problems if the valve assembly 204 is to be resheathed and redeployed.

In contrast to the prosthetic heart valve of FIG. 2A, the heart valve 200 of FIG. 2B exhibits low placement of the valve assembly 204 within the annulus section 240. Low placement of the valve assembly 204 enables the valve assembly to fully deploy when heart valve 200 is only partially deployed. As such, leaflets 208 reach their fully expanded and open positions during partial deployment and are able to function near normally, enabling a better assessment of the valve's functioning and final placement within the actual anatomy. Thus, if it appears that the valve needs to be moved, the heart valve 200 may be easily resheathed and repositioned. This concept is beneficial when dealing with less than ideal anatomical configurations.

The shape of the stent 202 during partial deployment will also affect the valve 204. If the stent shape is such that, while still partially retained by the sheath, it cannot open sufficiently to allow operation of the valve, it may not be possible to fully assess the operation of the valve in its intended placement position. Moreover, the height of the valve commissure features 216 relative to the inflow end 230 of the valve will affect the valve function. The lower the commissure features 216, meaning the closer to the inflow end 230, the more they will expand outwardly and the valve leaflets will be able to open during partial deployment, creating a flow passageway through the leaflets which approaches that of a fully deployed valve.

A transfemoral or transapical delivery device may be used to partially deploy the prosthetic heart valve such that an assessment may be made regarding flow through the valve and adequacy of coaptation. If, after the annulus section is unsheathed and the valve is tested, it is found that the valve needs to be repositioned, the annulus section may be resheathed and the valve redeployed as necessary.

Figure 3:
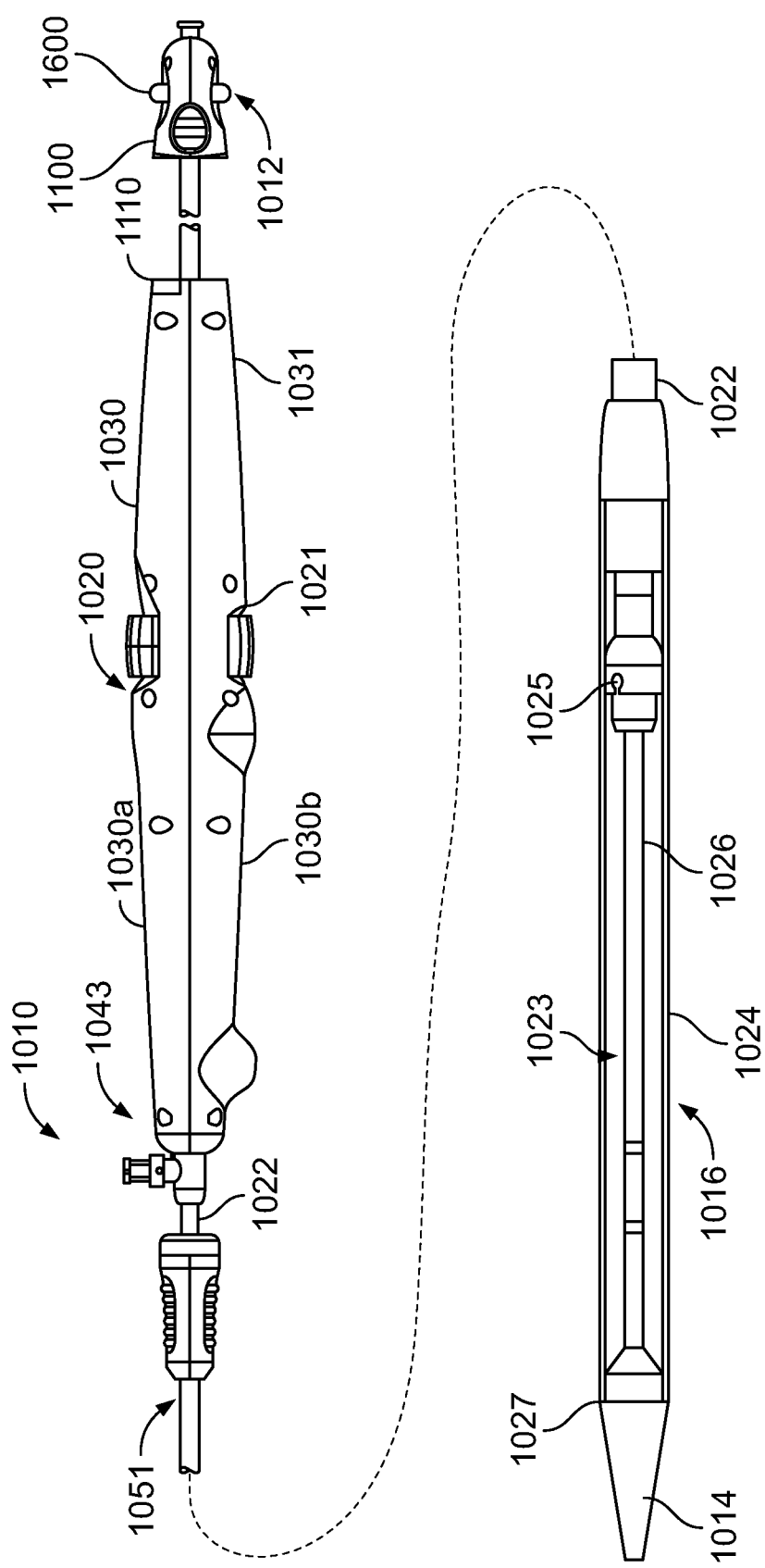
FIG. 3 is side view of an operating handle for a transfemoral delivery device for a collapsible prosthetic heart valve, shown with a side elevational view of the distal portion of a transfemoral catheter assembly.

Turning now to FIG. 3, an exemplary transfemoral delivery device 1010 for a collapsible prosthetic heart valve (or other types of self-expanding collapsible stents) has a catheter assembly 1016 for delivering the heart valve to and deploying the heart valve at a target location, and an operating handle 1020 for controlling deployment of the valve from the catheter assembly. The delivery device 1010 extends from a proximal end 1012 to a distal tip 1014. The catheter assembly 1016 is adapted to receive a collapsible prosthetic heart valve (not shown) in a compartment 1023 defined around an inner shaft 1026 and covered by a distal sheath 1024. The inner shaft 1026 extends through the operating handle 1020 to the distal tip 1014 of the delivery device, and includes a retainer 1025 affixed thereto at a spaced distance from distal tip 1014 and adapted to hold a collapsible prosthetic valve in the compartment 1023.

The distal sheath 1024 surrounds the inner shaft 1026 and is slidable relative to the inner shaft such that it can selectively cover or uncover the compartment 1023. The distal sheath 1024 is affixed at its proximal end to an outer shaft 1022, the proximal end of which is connected to the operating handle 1020. The distal end 1027 of the distal sheath 1024 abuts the distal tip 1014 when the distal sheath fully covers the compartment 1023, and is spaced apart from the distal tip 1014 when the compartment 1023 is at least partially uncovered.

The operating handle 1020 is adapted to control deployment of a prosthetic valve located in the compartment 1023 by permitting a user to selectively slide the outer shaft 1022 proximally or distally relative to the inner shaft 1026, or to slide the inner shaft 1026 relative to the outer shaft 1022, thereby respectively uncovering or covering the compartment with the distal sheath 1024. Operating handle 1020 includes frame 1030 which extends from a proximal end 1031 to a distal end and includes a top frame portion 1030a and a bottom frame portion 1030b. The proximal end of the inner shaft 1026 is coupled to a hub 1100, and the proximal end of the outer shaft 1022 is affixed to a carriage assembly within the frame 1030 that is slidable within the operating handle along a longitudinal axis of the frame 1030, such that a user can selectively slide the outer shaft relative to the inner shaft by sliding the carriage assembly relative to the frame. Alternatively, inner shaft 1026 may be actuated via hub 1100 to cover or uncover the compartment, for example for rapid covering or uncovering of the compartment 1023. Optionally, a stability sheath 1051 is disposed over some or all of outer shaft 1022. The stability sheath 1051 may be attached to the outer shaft 1022 or may be unattached. Additionally, stability sheath 1051 may be disposed over a majority of outer shaft 1022 or over a minority of the outer shaft (e.g., over 49% or less, over 33%, etc.). Optionally, stability sheath 1051 may be more rigid than outer shaft 1022.

Additionally, hub 1100 may include a pair of buttons, each attached to a clip. These clips on hub 1100 may mate with voids on frame 1030 to ensure that the hub and the frame are securely coupled together. Optionally, hub 1100 may also include a wheel 1600 which may assist in reducing strain in the distal sheath 1024 when loading the prosthetic heart valve into the delivery device 1010.

A first mechanism for covering and uncovering the compartment 1023 will be referred to as a "fine" technique as covering and uncovering occurs slowly with a high degree of precision. The "fine" movement may be provided by rotating a deployment wheel or actuator 1021, which may cause the carriage to pull or push the outer sheath 1022 (and thus the distal sheath 1024) proximally or distally. The second mechanism for covering and uncovering the compartment 1023 may be referred to as a "coarse" technique, by pulling or pushing the hub 1100 as described above. The "coarse" technique may be particularly suited for use when a prosthetic heart valve is not positioned within the compartment 1023. The delivery device may also include a resheathing lock 1043, which may restrict motion of the distal sheath 1024 once full deployment of the prosthetic heart valve is imminent. The resheathing lock 1043 may be disengaged when the desired position of the prosthetic heart valve is confirmed, so that the distal sheath 1024 may be further retracted to full release the prosthetic heart valve. In other words, the resheathing lock 1043 may help prevent unintentional or premature complete deployment of the prosthetic heart valve. Additional features of the delivery device 1010, for example including the function of wheel 1600, are described in greater detail in U.S. Patent Publication No. 2018/0153693, the disclosure of which is hereby incorporated by reference herein.

As noted above, it is often desirable for the commissures of the prosthetic heart valve to align rotationally with the commissures of the native heart valve upon deployment and/or implantation of the prosthetic heart valve into the native heart valve. Generally, such alignment may be approached from an active or passive standpoint. Active alignment generally refers to the inclusion of some mechanism that the user can activate or otherwise actively use to increase the likelihood of commissure alignment, for example by actively rotating the prosthetic heart valve until the prosthetic commissures are rotationally aligned with the native commissures. Passive alignment, on the other hand, generally referrers to the inclusion of some mechanism or design that allows the prosthetic heart valve commissures to rotationally align with the native heart valve commissures without the user actively inducing such alignment. The description below generally focuses on active commissure-to-commissure alignment mechanisms and designs. It should be understood that although various active commissure-to-commissure alignment mechanisms are described below, more than one of the mechanisms may be provided in a single system, and such designs may be combined with passive commissure-to-commissure alignment mechanism.

Certain embodiment below focus on mechanisms that allow a user to actively rotate the prosthetic heart valve (e.g. via rotation of a capsule in which the prosthetic heart valve is maintained during delivery). Some of the embodiments may include mechanisms for translating axial motion into rotational motion. In at least some of the embodiments disclosed above, mechanisms are described that allow for rotation (or torsion or twisting) to occur at or near the valve capsule or compartment 1023 based on axial movement elsewhere in the delivery device 1010. This may be generally preferable, particularly when the delivery device 1010 has a long catheter assembly (e.g. as may be seen in transfemoral delivery systems), as limiting rotation/torsion to occur at or near the valve compartment 1023 may allow for highly efficient transfer of energy, compared for example to rotating the entire catheter assembly in order to achieve rotation of the valve capsule or compartment 1023 at or near the distal end of the delivery device 1010. However, it should be understood that the rotation need not be limited to at or adjacent the valve compartment 1023 in other embodiments, as long as the desired valve rotation is achievable. In a number of the embodiments described below, the prosthetic heart valve 200 can achieve rotation in one or both of two ways. First, torsional force may cause material of delivery device 1010 (including portions near or adjacent the valve compartment 1023) to twist. Preferably, if this twisting occurs, the material(s) that is twisting has sufficient column strength to resist linear deformation. Suitable materials may include, for example, braided metals (such as stainless steel or nickel titanium alloys including nitinol), plastics, or combinations thereof. Second, the valve compartment 1023 and/or the retainer system (e.g. retainers 1025 and related structures, such as the hubs in which the retainers are formed) may include a mechanism that allows rotation of the valve compartment 1023 and/or the retainer system independent of other layers or portions of the delivery device 1010. For this independent rotation, it may be preferable that the valve compartment 1023 and/or the retainer system is directly attached to the rotational or torsional force mechanism, while being decoupled from the non-rotating layers or structures of the delivery device 1010. Whether one or both of the mechanisms described above is used, the delivery system 1010 may be inserted into the patient in a torqued or rotated condition, or a non-torqued or non-rotated condition. In either scenario, the direction of axial movement that results in the torqueing or rotation (or the alleviation of torque or reversal of rotation) will depend on the particular mechanism and the particular state in which the delivery device 1010 is inserted into the patient. Various examples of one or more of the above concepts are described in more detail below, but it should be understood that these are only examples, and further that one or more of these examples may be combined in a single system.

Figure 4A:
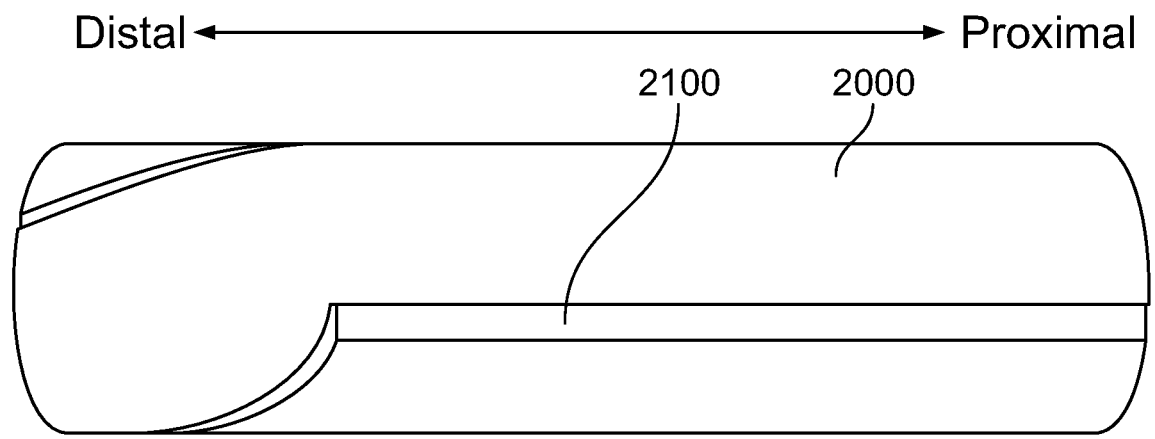
FIGS. 4A-B illustrate grooved portions of a cylindrical tube according to an embodiment of the disclosure.
Figure 4B:
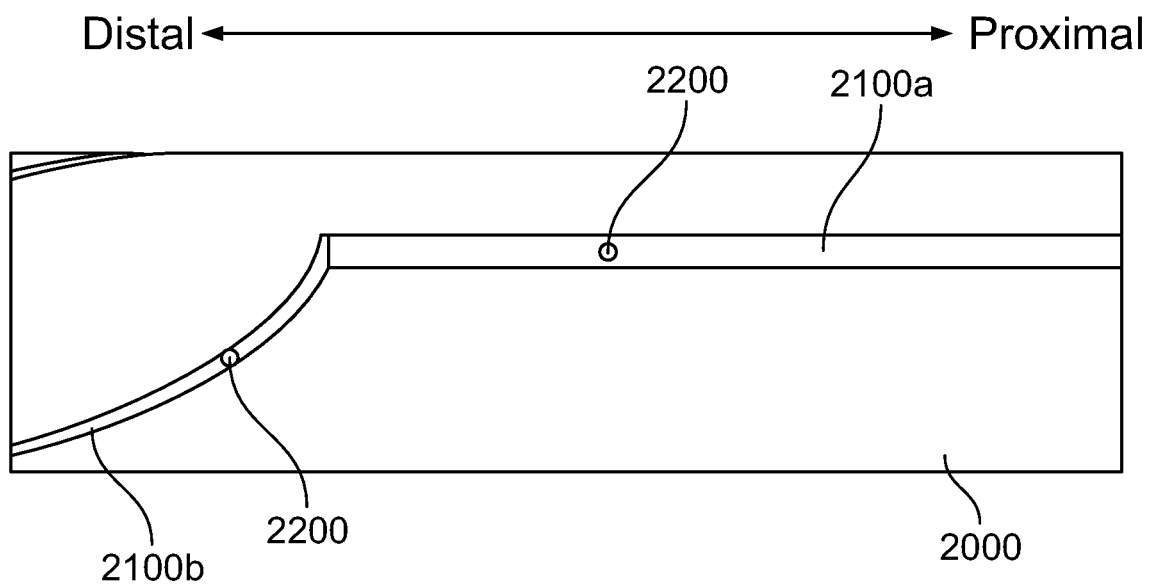

FIGS. 4A-B illustrate an exemplary mechanism that may be used with delivery device 1010 (or other delivery devices) to translate axial movement into rotational movement to actively align the commissures of a prosthetic heart valve with commissures of a native heart valve. The mechanism in FIGS. 4A-B utilizes pre-set grooves to prescribe torsion as the mechanism is advanced distally or pulled proximally. In particular, FIGS. 4A-B illustrate a generally cylindrical tube 2000 that includes a plurality of grooves 2100 or other indentations therein. In the illustrated embodiment, each groove 2100 includes a generally axial or linear portion 2100*a* that forms a proximal section of the groove, and a curved portion 2100*b* that forms a distal section of the groove, the linear portion 2100*a* and curved portion 2100*b* being continuous. These grooves 2100 may be formed by any suitable method, including subtractive manufacturing, for example milling, cutting, or otherwise removing a thickness of the outer surface of the tube 2000 to form recessed areas in the shape of grooves 2100. The tube 2000 may include one or more of the grooves 2100, and preferably the grooves are identical to one another in axial position and shape, with the grooves being substantially equally positioned around the circumference of the tube 2000. For example, two grooves 2100 may be provided separated about 180 degrees, three grooves 2100 may be provided separated by about 120 degrees, etc. It should become clear that the inclusion of multiple grooves may help with a smoother translation of axial movement into rotational movement, but as little as one groove may be suitable to achieve the desired functionality.

Not shown in FIGS. 4A-B is an outer sleeve that is positioned to overlie the cylindrical tube 2000 and to translate with respect to the cylindrical tube 2000. The outer sleeve may be cylindrical and hollow so that it may be positioned to overlie the cylindrical tube, and may include one or more tabs or protrusions 2200 on an interior surface thereof extending radially inwardly, with at least one protrusion for each groove 2100. One of the protrusions 2200 is illustrated in FIG. 4B within one of the grooves 2100, the protrusion 2200 being illustrated in two different positions of the outer sleeve relative to the cylindrical tube 2100. In use, as the outer sleeve is moved axially with respect to the cylindrical tube 2100, the outer sleeve only moves axially while the protrusion 2200 is positioned within the linear portion 2100*a* of the groove 2100. This corresponds to the relatively proximal position of protrusion 2200 illustrated in FIG. 4B. As axial movement of the outer sleeve continues, the protrusion 2200 will move from the linear portion 2100*a* of the groove 2100 to the curved portion 2100*b* of the groove 2100. Because the curved portion 2100*b* extends both in axial and circumferential directions, as the outer sleeve continues to advance distally, the protrusion 2200—and thus the outer sleeve—begins to rotate relative to the cylindrical tube 2000 as it continues moving axially. This corresponds to the relatively distal portion of protrusion n2200 illustrated in FIG. 4B.

Although illustrated in isolation in FIGS. 4A-B, the cylindrical tube 2000 may be incorporated into a delivery device, such as delivery device 1010. For example, the cylindrical tube 2000 may be provided at or adjacent the distal sheath 1024, with the outer sleeve described above being attached to the distal sheath 1024 and/or the retainer system (e.g. the proximal hub that includes retainers 1025) so that the user my advance or retract the outer sleeve relative to the cylindrical tube (for example via a wheel or other actuation mechanism in the handle operatively attached to the cylindrical tube 2000) to allow the user to force the valve compartment 1023 and/or the retainer system to rotate into a desired orientation. In order for both the outer sleeve and the cylindrical tube 2000 to stay fixed to the distal sheath 1024 (to maintain desired orientation during deployment), the subassembly containing cylindrical tube 2000 preferably is rotationally (but not axially) fixed relative to the handle 1020, and the outer sleeve and distal sheath 1024 (and/or retainer system) is preferably allowed to rotate freely relative to the handle 1020. The unsheathing action, in which the distal sheath 1024 is retracted proximally to allow the prosthetic heart valve 200 to deploy, may still be driven by proximal translation of the distal sheath 1024 relative to the handle 1020. In other words, the retraction of the distal sheath 1024 may be independent of the translation of the outer sleeve relative to the cylindrical tube 2000. With this configuration, a user may advance the outer sleeve relative to the cylindrical tube 2000 to cause the desired rotation of the outer sheath 1024 (and/or retainer system). Then, when the rotational alignment is achieved, the distal sheath 1024 (along with the outer sleeve and cylindrical tube 2000) may be withdrawn or retracted to allow the prosthetic heart valve 200 to deploy while it has the desired rotational orientation.

Although one particular example of grooves 2100 in the tube 2000 is illustrated in FIGS. 4A-B, it should be understood that the grooves may be altered to provide different amount of rotation and different torsion forces. For example, the farther the curved portion 2100b of the groove 2100 extends around the circumference of the tube 2000, the greater total amount of rotation will be available. Similarly, the total length of the curved portion 2100b of the groove 2100 may be adjusted (in the axial direction) to provide a desired amount of torsion. If the curved portion 2100b extends over a relatively small axial distance, the torsion force will be greater than if the same amount of curvature is provided over a longer axial distance. These parameters may be adjusted to meet the particular desired degree of rotation and amount of torsion that may be applied by the user to rotate the prosthetic heart valve 200 to align the prosthetic commissures with the native commissures prior to (or during) deployment of the prosthetic heart valve from the delivery device 1010.

Figure 5A:
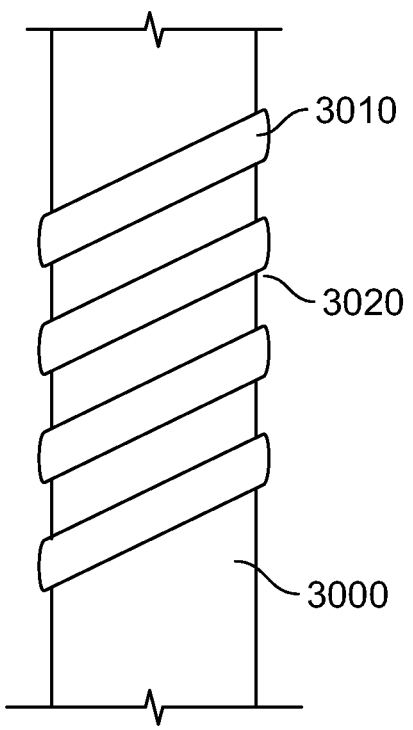
FIG. 5A is a highly schematic side view of a worm screw feature on a shaft component of a delivery device.
Figure 5B:
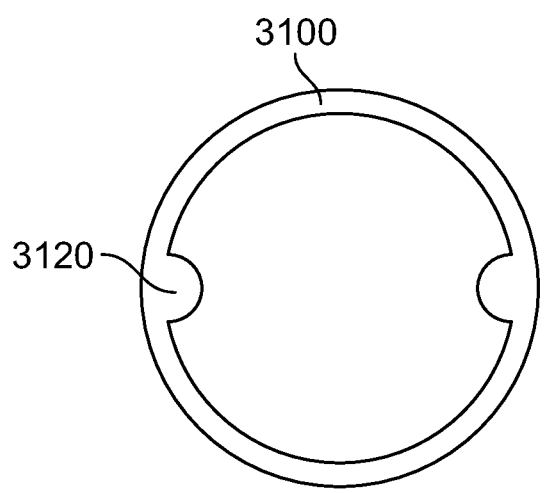
FIG. 5B is a cross-section of a tabbed outer sheath adapted to engage the worm screw feature of FIG. 5A.
Figure 5C:
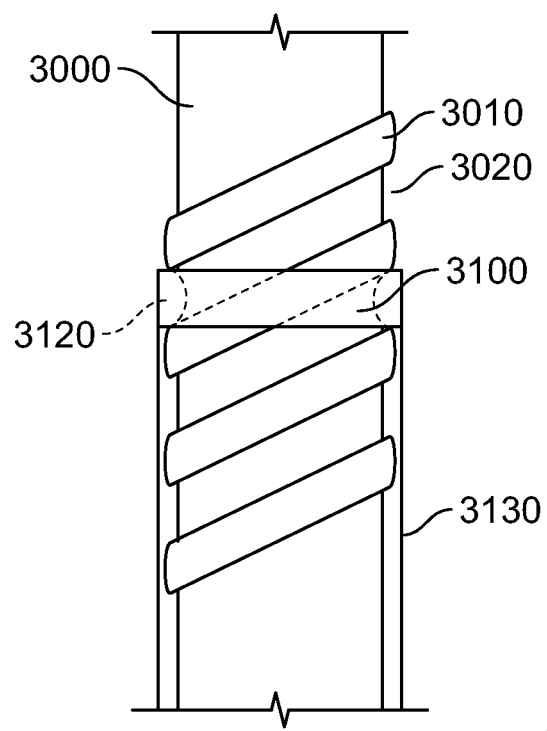
FIG. 5C is a highly schematic side view of the outer sheath of FIG. 5B assembled to the shaft of FIG. 5A.

FIGS. 5A-C illustrate another embodiment for providing active rotation of prosthetic heart valve 200 while it is within the valve compartment 1023. For example, FIG. 5A illustrates a shaft 3000 that includes threading, a worm gear, or the like. In the illustrated embodiment, the shaft 3000 includes one or more threads 3010 that form a worm gear structure, the threads 3010 extending radially outwardly from the shaft 3000 and defining spaces 3020 between adjacent threads 3010. Although shaft 3000 is illustrates about four revolutions of the thread 3010, it should be understood that more or fewer revolutions may be provided. FIG. 5B illustrates an overlying sleeve or sheath 3100 that may be positioned over shaft 3000. The sheath 3100 may include one or more tabs or protrusions 3120 extending radially inwardly from a wall of the sheath 3100. The protrusions 3120 are preferably sized, shaped, and positioned to fit within spaces 3020 between adjacent threads 3010 of the shaft 3000, similar to a ball screw structure. Although the sheath 3100 is illustrated with two hemispherical protrusions spaced about 180 degrees apart, it should be understood that more or fewer protrusions may be provided, and may be provided in different shapes, as long as the protrusions 3120 are configured to interact with threads 3010 of the shaft 3000.

As shown in FIG. 5C, when the sheath 3100 is positioned over the shaft 3000, the protrusions 3120 intermesh with the threads 3010 of the shaft 3000. The sheath 3100 may be provided with one or more pull wires 3130 that may be pulled to draw the sheath 3100 toward the user. For example, the pull wires 3130 may be coupled to the handle 1020 of the delivery device 1010, including for example via a knob actuator that may be turned or a slide actuator that may be slid proximally to pull the pull wires 3130. As the user applies proximal force on the pull wires 3130, the intermeshing of the protrusions 3120 with the threads 3010 forces the shaft 3000 to rotate as the sheath 3100 is translates axially. Although the sheath 3100 is illustrated in FIG. 5C as having a short length (e.g. only about as long as the length of one of the spaces 3020), the sheath 3100 may be provided as a substantially longer sheath, extending partially, mostly, or entirely back to the handle 2020. For example, the sheath 3100 may include one or more pull-wire lumens extending through the wall of the sheath 3100 to guide the pull wires 3130 back to the handle 2020 or another location where the pull-wires can be manipulated. In some embodiments, the sheath 3100 may be formed as one or more of a laser cut hypotube, an optimized braided composite shaft, a multi-layer coil, and/or helical hollow strand tubing, which hay help ensure that the sheath 3100 forces rotation of the shaft 3000, as opposed to the shaft 3000 forcing rotation of the sheath 3100, during relative axial translation.

The shaft 3000 is preferably operably coupled to the valve compartment 1023 so that, if a user determines that the valve compartment 1023 (and/or the retainer system) needs to be rotated in order to align the prosthetic commissures with the native commissures, the user may pull on the pull wires 3130 until the shaft 3000 (and thus the valve compartment 1023 and/or retainer system) rotates to the desired amount, resulting in commissure-to-commissure alignment. For example, the worm gear (or threads 3010) may be provided on an outer surface of the outer shaft 1022 at or near (e.g. just proximal to) the distal sheath 1024, with the overlying sheath 3100 provided as an additional and separately movable structure. With this configuration, shaft 3000 is actually a portion of outer shaft 1022 near the distal sheath 1024. Thus, the axial translation of the outer sheath 3100, and thus the rotation of the shaft 3000 and valve capsule 1023 (and/or the interior retainer system) may be independent of the axial translation of the distal sheath 1024 to deploy the prosthetic heart valve 200. This configuration may allow for the desired rotational orientation of the prosthetic heart valve 200 to be achieved in a step that is independent of the valve deployment step.

In another embodiment, axial translation may be translated into rotational motion of the valve compartment 1023 (and/or the interior retainer system) via discrete amounts, with a single axial actuation producing a corresponding amount of rotation. In one example, the mechanism may have structure similar to a "click pen" configuration. With this configuration, a plunger 4200 and a cam 4000 may interact so that, as the plunger 4200 is translated in each discrete step, the cam 4200 is rotated a discrete amount. For example, referring to FIGS. 6A-B, the plunger 4200 may include one or more distal extensions with angled teeth 4220, and the cam 4000 may include angled teeth 4020 that confront the angled teeth 4220 of the plunger 4200. Springs or other biasing members may be provided on each side of the mechanism.

Figures 6A, 6B:
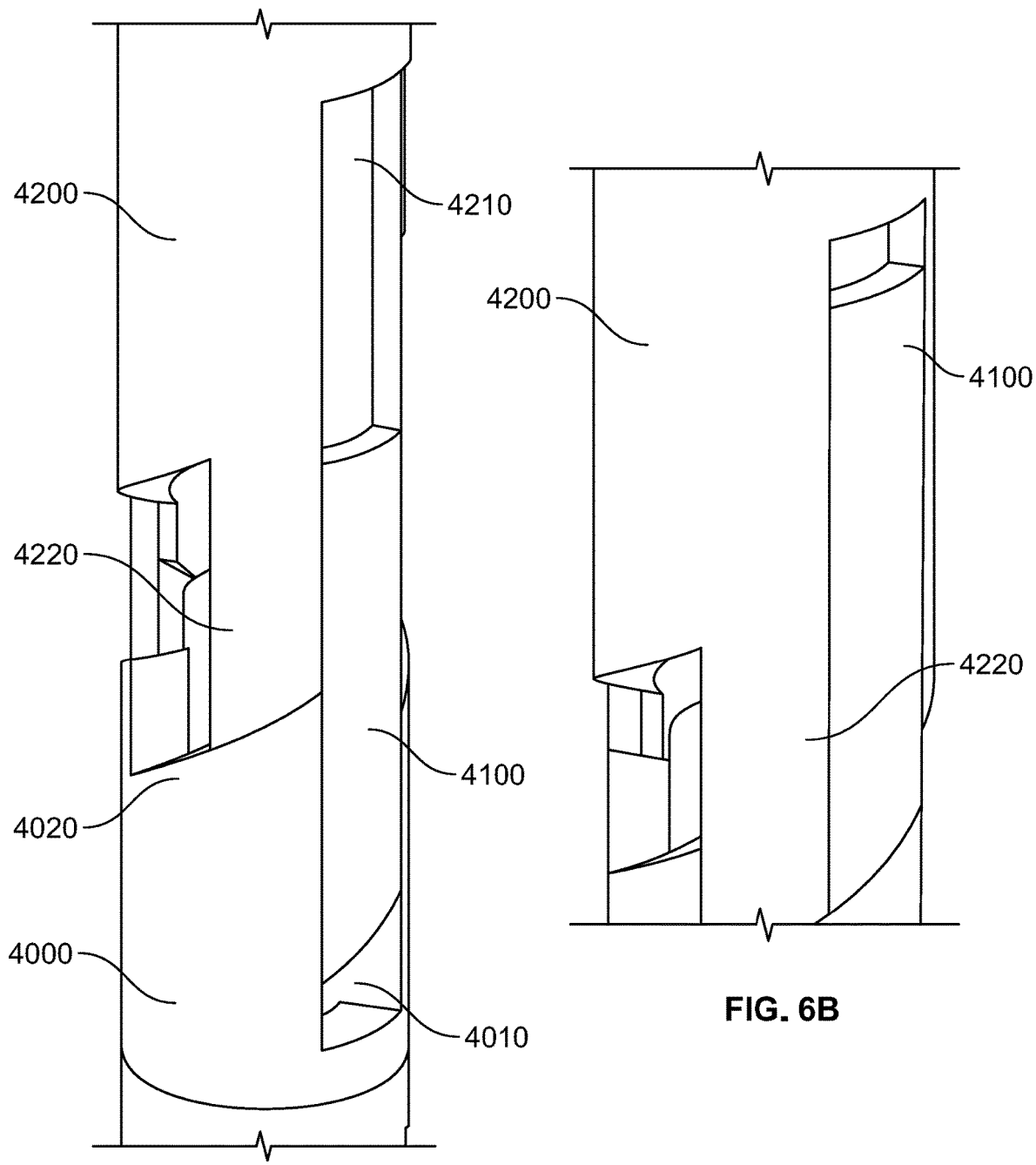
FIGS. 6A-B are highly schematic illustrations of a plunger and cam mechanism in two different rotational states relative to each other.

Referring to FIG. 6A, springs (not illustrated) or other biasing members may be positioned on opposite ends of the plunger 4200 and the cam 4000 so that the two components are always pressing against each other. The plunger 4200 may include a guide slot 4210 (which may be generally rectangular), and the cam 4000 may also include a guide slot 4010 (which may be generally rectangular). A guide member 4100, which may include an angled tooth at its distal end, may be positioned on the interior of a sheath that overlies part of or all of the plunger 4200 and cam 4000 mechanisms. Thus, although guide member 4100 is illustrated as a standalone component in FIGS. 6A-B, it should be understood that this is for purposes of illustration only, and the guide member 4100 may be integral with an overlying sheath. In the position illustrated in FIG. 6A, the angled tooth 4220 of plunger 4200 rests on an upper half of a corresponding angled tooth 4020 of cam 4000. The biasing forces tend to forces the angled tooth 4220 to slide along the angled tooth 4020 when in this position (e.g. to the left in the view of FIG. 6A), but the guide member 4100 being received in both guide slots 4210 and 4010 prevent such rotation. If the plunger 4200 is depressed distally (downward in the views of FIGS. 6A-B), the plunger 4200 and cam 4000 move in unison axially relative to guide member 4100, until the angled distal end of the guide member 4100 clears the top of the guide slot 4010 in the cam 4000. Once the guide member 4100 is clear of the guide slot 4010 in the cam 4000, there is nothing stopping the angled tooth 4220 of plunger 4200 from completely sliding down the angled tooth 4020 of the cam 4200. Thus, after depressing the plunger 4200 from the position shown in FIG. 6A, the plunger 4200 and the guide member 4100 will both rotate in unison relative to the cam member 4000, to the position shown in FIG. 6B. Thus, the type of plunger and cam mechanism shown and described in connection with FIGS. 6A-B may allow for discrete axial movements (e.g. depression of the plunger 4200) to cause discrete rotational movements (e.g. rotation of cam 4000). As with other embodiments described herein, this mechanism may be provided in delivery device 1010, for example with the cam 4000 operatively coupled to the distal sheath 1024 (and/or the retainer system), so that the prosthetic heart valve 200 within the distal sheath 1024 may be actively rotated at discrete rotational intervals to align the prosthetic commissures with the native commissures prior to deploying the prosthetic heart valve 200. Examples of other structures that may be suitable in this "click pen" type of configuration are described in greater detail in U.S. Pat. No. 3,205,863, the disclosure of which is hereby incorporated by reference herein.

Figure 7A:
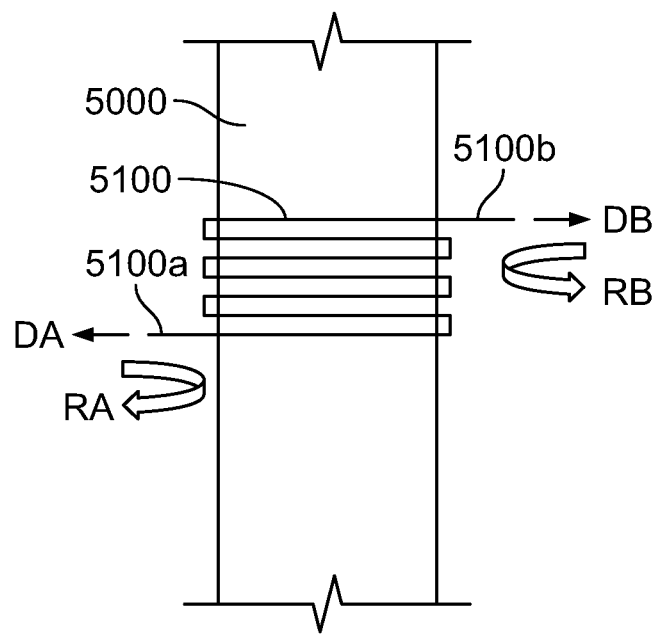
FIG. 7A is a highly schematic side view of a bi-directional pull-wire feature on a shaft component of a delivery device.
Figure 7B:
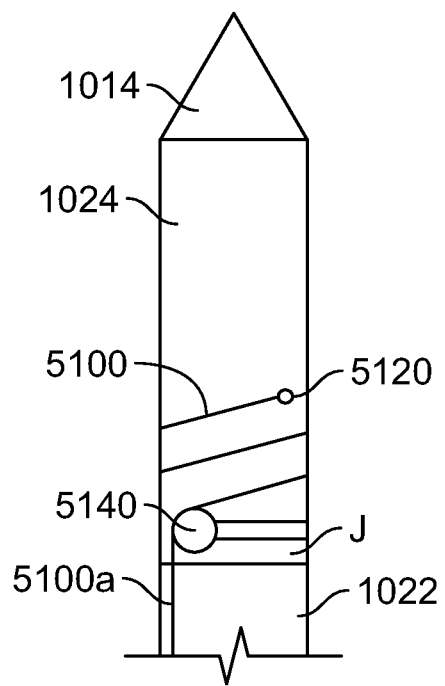
FIG. 7B is a highly schematic side view of a uni-directional pull-wire feature on a shaft component of a delivery device.

In still another embodiment, a pull string or wire may be wrapped around a cylindrical member so that, as the pull string is pulled axially, the pull string forces rotation of the cylindrical member. For example, FIG. 7A illustrates a shaft 5000, which is preferably a cylindrical member. Also shown in FIG. 7A is a schematic illustration of a pull wire 5100 that has two opposite free ends, with a middle portion of the pull wire 5100 being wrapped around the shaft 5000. The two free ends of the pull wire 5100 may extend proximally, for example to or near the handle 1020. With this configuration either end of the pull wire 5100 may be pulled in order to rotate the shaft 5000, with the direction of rotation depending on which end of the pull wire 5100 is pulled. For example, if a first end 5100a of pull wire 5100 is pulled in direction DA, the shaft 5000 may rotate in a first direction RA. On the other hand, if a second end 5100b of pull wire 5100 is pulled in direction DB, the shaft 5000 may rotate in a second direction RB. In some embodiments, the pull wire 5100 may be wrapped around the shaft 5000 tightly so that friction will induce the rotation when the pull wire 5100 is pulled. Although not illustrated in FIG. 7A, one or both ends of the 5100a-b of the pull wire 5100 may be redirected axially toward the handle 1020. In some embodiments, a bearing or joint may be provided proximal to the location where the pull wire 5100 is wrapped around the shaft 5000 to assist in the rotation of shaft 5000. Examples of such bearing or joints are described in greater detail in connection with FIGS. 11A-B below. Although FIG. 7A illustrates a pull wire 5100 in which two ends 5100a, 5100b may be pulled to provide rotation in opposite directions, it should be understood that a pull wire instead may include a first end fixed to the shaft 5000, with the second end being the only end available to the user for pulling. While this alternate embodiment may only allow rotation in a single rotational direction upon pulling the wire, the mechanism may be relatively simpler than that shown in FIG. 7A. For example, FIG. 7B illustrates a similar configuration but where pull wire 5100 has a first end fixed to the shaft (in this case illustrated as distal sheath 1024) at a fixation point 5120, and a middle portion of the pull wire 5100 being wrapped around the distal sheath 1024. The pull wire 5100 is routed along a pulley mechanism 5140 to redirect the end 5100a of the pull wire 5100 axially toward the handle 1020 of the delivery device 1010. Also illustrated in FIG. 7B is a joint J such as a thrust bearing between the outer shaft 1022 and the distal sheath 1024, similar or identical to that shown an described in connection with FIGS. 11A-B. A joint J and/or one or more pulley mechanisms (or other structures that provide redirection of the pull wire 5100) may similarly be used in the embodiment of FIG. 7A. The embodiments shown and described in connection with FIGS. 7A-B may provide similar functionality, albeit via different mechanisms, as the embodiment described in connection with FIGS. 5A-C, with a main functional difference being that the embodiment of FIG. 7A may provide for bi-directional rotation while the embodiments of FIGS. 5A-C and 7B may provide unidirectional rotation. Otherwise, the use of a delivery device that includes shaft 5000 and pull wire 5100 may be substantially similar to that described above in connection with the shaft 3000 of FIGS. 5A-C.

Figure 8:
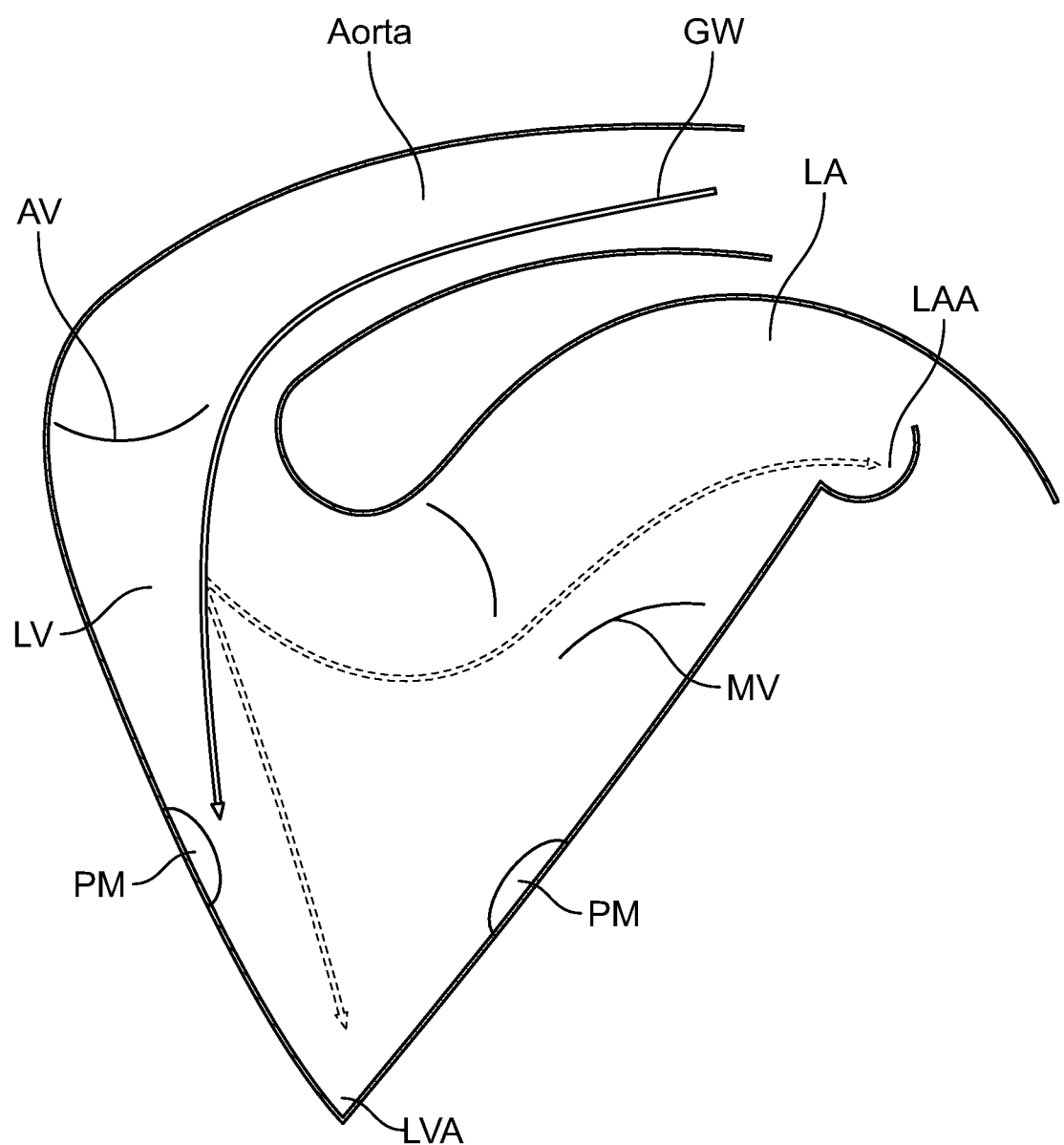
FIG. 8 is a highly schematic cross-section of a heart illustrating various anchoring points for a guidewire.

In other embodiments of the disclosure, described in greater detail below, one or more guidewires may be used to assist in rotating the prosthetic heart valve 200 relative to the native valve annulus to align the prosthetic commissures with the native commissures prior to (and/or during) deployment of the prosthetic heart valve 200. These mechanisms may achieve this relative rotation by rotating the prosthetic heart valve, by reorienting the heart itself (albeit such reorientation may only be slight), or both. In order to use one or more guidewires to assist with such active commissure-to-commissure alignment, it may be important to be able to anchor the guidewire (e.g. a distal end of the guidewire) to tissue of the heart. Any suitable anchoring location may be utilized, and some exemplary anchoring locations are illustrated in FIG. 8. FIG. 8 illustrates a guidewire GW that has been passed into a patient's heart via the aorta and through the aortic valve AV into the left ventricle LV. In this particular illustration, three anchoring locations for the guidewire GW are illustrated. The guidewire GW is illustrated as having a distal end anchored to a papillary muscle PM, although it should be understood that other papillary muscles in the heart may be suitable anchor points in addition to the one illustrated. FIG. 8 illustrates a second potential anchoring point of the guidewire GW being the left ventricular apex LVA (with the guidewire GW positioning illustrated with a broken line in this second anchoring location). FIG. 8 illustrates a third potential anchoring point of the guidewire GW being the left atria appendage LAA within the left atrium LA (with the guidewire GW positioning illustrated with a broken line passing through the mitral valve MV in this third anchoring location). Regardless of where the distal end of the guidewire GW is anchored, it should be understood that a proximal portion of the guidewire GW (not illustrated in FIG. 8) may be stabilized by the delivery device 1010 or some separate fixture. The particular way in which the distal end of the guidewire GW is anchored to the particular anchoring point may be dependent, at least in part, on which anchoring point is used. For example, the distal end of the guidewire GW may be provided with a screw, fish-hook, or other piercing or puncturing feature that may pierce, puncture, or otherwise engage tissue to anchor the guidewire GW. In one example, the piercing or puncturing mechanism may be particularly well suited when the anchoring location is one of the papillary muscles PM. In another embodiment, the distal end of the guidewire GW may be provided with a coil-shape which may be able to lodge into an anchoring location, such as the left ventricular apex LVA. In still further embodiments, the distal end of the guidewire GW may be provided with an expandable feature such as an expandable balloon, which may be passed into the left atrial appendage LAA and expanded to provide the desired anchoring. However, it should be understood that any suitable anchoring mechanism may be provided for any desired anchoring location. In other embodiments, the guidewire GW may puncture through the left ventricle (e.g. at or near the left ventricular apex LVA), and an anchor may be deployed on an epicardial surface of the heart. In these embodiments, the distal end of the guidewire GW may be provided with an expandable anchor, for example an expandable anchor formed of braided or mesh nitinol wires, with the anchor having a small profile when collapsed to pass through an incision or puncture in the ventricular wall, and then to expand to a larger profile after passing through the ventricular wall. Collapsible anchoring structures that may be suitable for epicardial anchoring are described in greater detail in U.S. Patent Publication No. 2021/0169645, the disclosure of which is hereby incorporated by reference herein. Various embodiments are described below that use a coil anchoring mechanism, but it should be understood that other anchoring mechanisms may be used instead of the illustrated coil anchoring mechanism, as described above.

FIG. 9A illustrates a guidewire 7000 according to an aspect of the disclosure. In FIG. 9A, only a distal end of guidewire 7000 is illustrated, for example the portion of the guidewire that will pass through the aortic arch and into the left ventricle in a transfemoral approach. Guidewire 7000 may be conceptually divided into three general portions, including a pre-annulus section 7100, and annulus section 7200, and a post-annulus section 7300. When guidewire 7000 is in an anchored condition, the annulus section may traverse the annulus of the aortic valve AV. The post-annulus section 7200 may include an anchoring coil 7210, which may for example be sized and shaped to lodge into the left ventricular apex LVA in order to anchor the distal end of the guidewire 7000 to the heart. However, as noted above, other anchoring mechanisms besides an anchoring coil 7210 may be suitable for use with guidewire 7000, and other anchoring locations besides the left ventricular apex LVA may be suitable. The pre-annulus section 7100 preferably has a non-circular cross-section, with the delivery device 1010 having an internal guidewire lumen with a corresponding shape. It should be understood that, despite the annulus section 7200 having a non-circular cross-section (as described in greater detail below), in some embodiments the pre-annulus section 7100 may have a circular cross section. However, if the pre-annulus section 7100 does have a non-circular cross section, it may provide for "clocking" or a known and/or predetermined rotational orientation of the delivery device 1010 relative to the guidewire 7000 when the delivery device is initially slid over the guidewire 7000.

FIG. 9B illustrates an enlarged isolated view of the annulus section 7200 of FIG. 9A. As noted above, the annulus section 7200 may be positioned to traverse the native aortic valve annulus when the guidewire 7000 is in an anchored condition (e.g. with anchoring coil 7210 lodged within the left ventricular apex LVA). Preferably, the annulus section 7200 is formed to have a relatively high stiffness. As will become clear below, the stiffness of the annulus section 7200 may help force rotation of a portion of the delivery device 1010 (e.g. the distal sheath 1024) as it passes over the annulus section 7200. Although it should be noted that the entire guidewire 7000 (both the annulus section 7000 and the other sections) preferably has a high enough stiffness to resist rotation as the delivery device passes over the annulus section 7200, as described in greater detail below. In order to assist with forcing rotation of the distal sheath 1024 of the delivery device 1010 as the distal sheath 1024 advances distally over the annulus portion 7200, the annulus portion 7200 may incorporate a twist. FIG. 9C illustrates a cross-section of the annulus portion 7200 taken along the line 9C-9C of FIG. 9B. As shown in FIG. 9C, the annulus section 7200 may have a non-circular cross-section that twists along the distance of the annulus section 7200. For example, the annulus section 7200 may have a substantially oval or elliptical cross-section, with the orientation of the major axis being in different rotational positions (e.g. so that the annulus section 7200 twists) along the distance of the annulus section 7200. The pre-annulus section 7100 may have a similar or identical cross-sectional shape as the annulus section 7200. In this particular example, the delivery device 1010 may include an inner guidewire lumen with a corresponding cross-section (e.g. oval or elliptical), so that the delivery device is not capable of freely rotating about the guidewire 7000. In use, the guidewire 7000 may first be advanced into the patient's heart (e.g. via a transfemoral approach through the aorta, through the aortic valve AV, and into the left ventricle LV, with the coiled anchor section 7210 being lodged in the left ventricular apex LVA to anchor the distal end of the guidewire 7000. Then, the delivery device 1010 may be advanced over the guidewire 7000, for example by positioning an interior guidewire lumen of the delivery device 1010 over a proximal end of the guidewire 7000, and then advancing the delivery device 1010 distally until the distal end of the delivery device 1010 is near the annulus section 7200. Preferably, a proximal portion of the guidewire 7000 is stabilized, for example via a fixture outside the patient, so that any forces applied to the guidewire 7000 from the delivery device 1010 do not significantly change the position or orientation of the guidewire 7000. As the delivery device 1010 advances over the annulus portion 7200, the portion of the delivery device 1010 overlying the annulus portion 7200 will begin to rotate, at least in part because the non-circular cross-sections of the annulus portion 7200 and the internal guidewire lumen prevent free rotation of the delivery device over the guidewire 7000. The stiffness of the annulus section 7200 (and/or the stiffness of the remaining portions of the guidewire 7000), as well as the anchoring of the distal end of the guidewire 7000 (and the stabilization of proximal portions of the guidewire 7000) helps to ensure that the annulus section 7200 substantially retains its rotational orientation relative to the annulus of the aortic valve AV, as opposed to the delivery device 1010 forcing the guidewire 7000 to rotate. The curvature and/or twist of the annulus section 7200 may allow for significant enough rotation over a short enough distance so that the distal sheath 1024 (and/or the retainer system) may have enough range of rotation within a short distance so that the desired rotational orientation of the prosthetic heart valve 200 may be achieved while maintaining a desired range of axial positions of the distal sheath 1024 with respect to the native annulus. In other words, the desired rotational position of the prosthetic heart valve 200 may be achieved without compromising a desired axial position of the prosthetic heart valve 200 with respect to the native valve annulus.

Figure 10A:
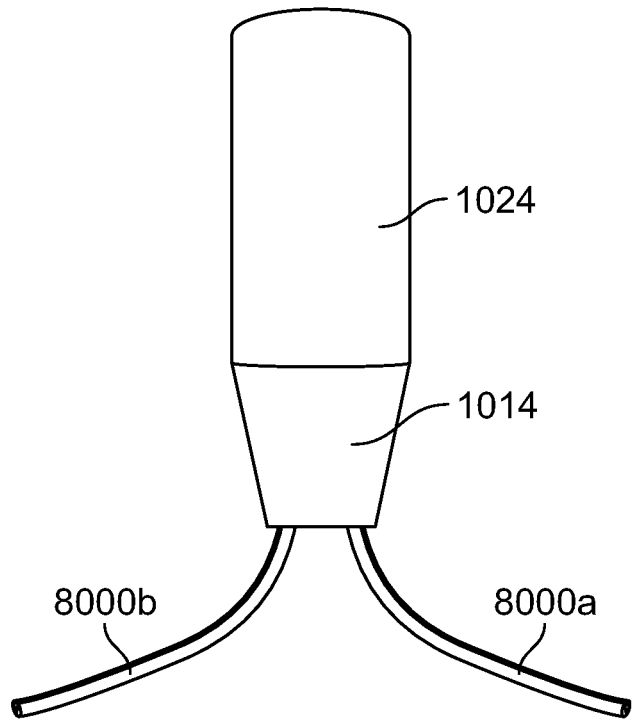
FIGS. 10A-B are front and perspective views, respectively, of a distal end of a delivery device over a double guidewire system.
Figure 10B:
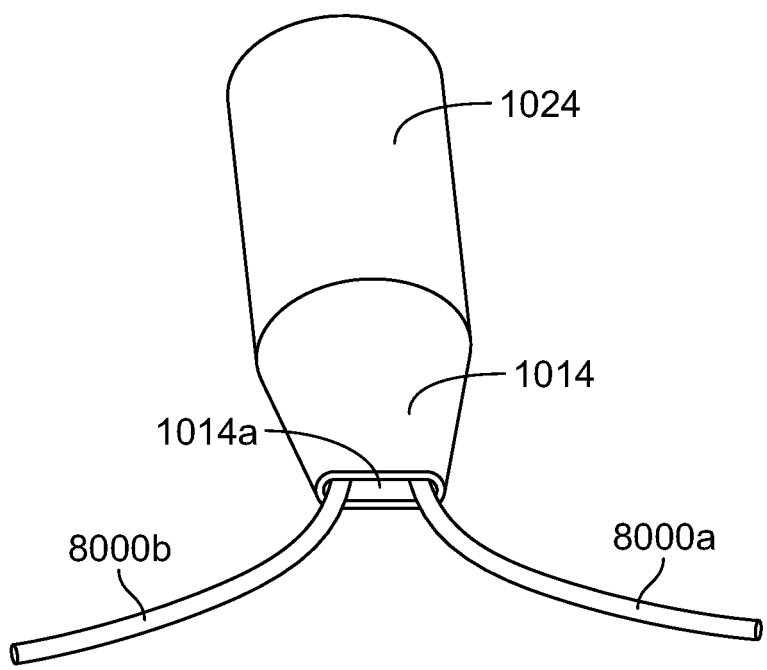

In another embodiment of the disclosure, a pair of guidewires 8000*a-b* may be used to in order to achieve a desired rotational position of the prosthetic heart valve prior to (or during) deployment. For example, FIGS. 10A-B illustrate a system that includes a first guidewire 8000*a* and a second guidewire 8000*b*. In the illustrated embodiment, each guidewire 8000*a-b* is substantially similar or identical, for example having a generally circular cross-section of about equal diameters. Each individual guidewire 8000*a-b* may be anchored to a desired location in the heart using any of the above-described techniques, for example via piercing or hooking the distal end of each guidewire 8000*a-b* into the same or different papillary muscles PM. With the guidewires 8000*a-b* anchored in the heart (and preferably while maintaining the proximal ends of the guidewires 8000*a-b* in a stabile configuration, for example with a fixture), the delivery device 1010 may be advanced over the pair of guidewires 8000*a-b*. In the illustrated example, instead of having an internal guidewire lumen that closely or exactly matches the shape a single guidewire, the delivery device 1010 may include a guidewire lumen 1014*a* that may be oval or elliptical. For example, as best shown in FIG. 10B, if each guidewire 8000*a-b* has a circular cross-section and about the same diameter, the guidewire lumen 1014*a* may have a rectangular or obround shape that had a width about equal to the diameter of the guidewires 8000*a-b*, but a length that is at least twice as large as the diameter of the guidewires 8000*a-b*. With this configuration, there are only two possible rotational orientations of the delivery device 1010 with respect to the guidewires 8000*a-b*, and the particular rotational orientation may be determined based on how the delivery device 1010 is inserted over the guidewires 8000*a-b*. Once the guidewires 8000*a-b* are both within the guidewire lumen 1014*a*, the rotational orientation of the delivery device 1010 with respect to the guidewires 8000*a-b* may be substantially fixed. Because the delivery device 1010 will be rotationally locked relative to the guidewires 8000*a-b*, and because the positions of the guidewires 8000*a-b* within the heart will be known prior to advancing the delivery device 1010 over the guidewires 8000*a-b*, the prosthetic heart valve 200 may be loaded into the capsule 1023 with a particular orientation so that, when the capsule 1023 is within or adjacent the native valve annulus, the prosthetic commissures will rotationally align with the native commissures.

It should be understood that similar configurations to that shown in FIGS. 10A-B may be used without departing from the scope of the disclosure. For example, the two guidewires 8000*a-b* may be provided with different sizes and the guidewire lumen 1014 may be provided with corresponding sizes so that there is only one possible rotational orientation of the delivery device with respect to the guidewires 8000*a-b*. Still further, instead of having a single guidewire lumen 1014*a* in which both guidewires 8000*a-b* can be received, the guidewire lumen 1014*a* may be provided as two separate lumens that match the sizes of the two guidewires, whether those sizes are the same or different.

Figure 11A:
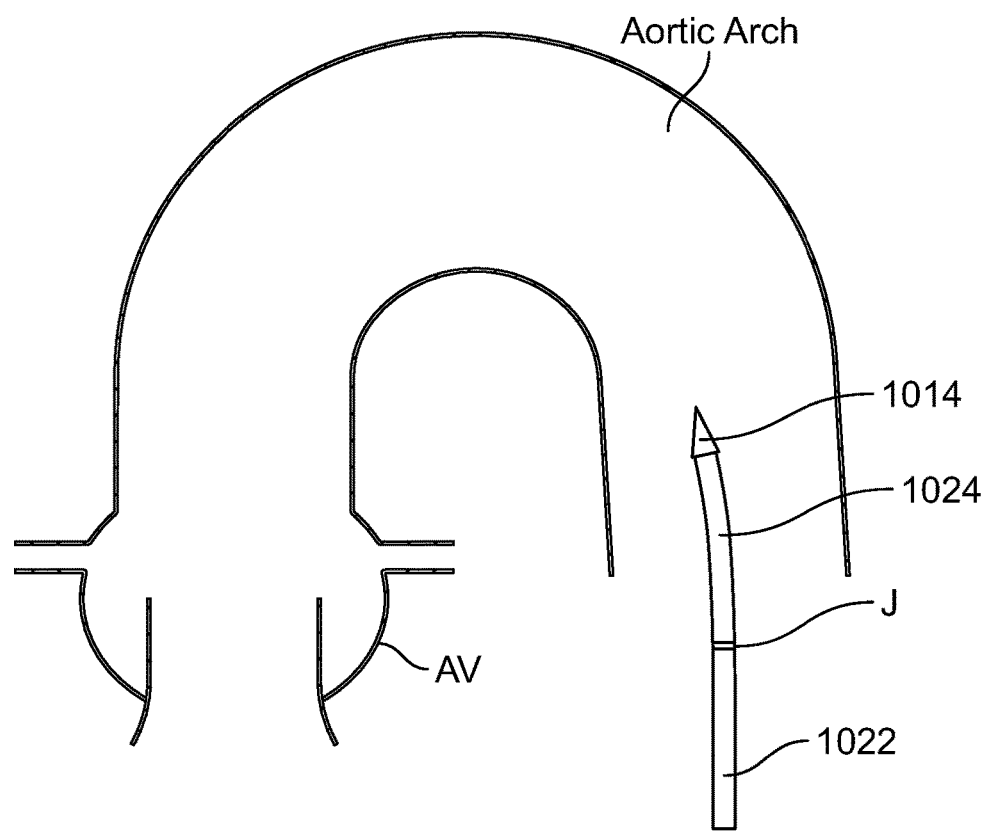
FIG. 11A is a highly schematic side view of a transfemoral delivery device traversing the aortic arch, with a distal end of the delivery device being rotatable relative to another portion of the delivery device.
Figure 11B:
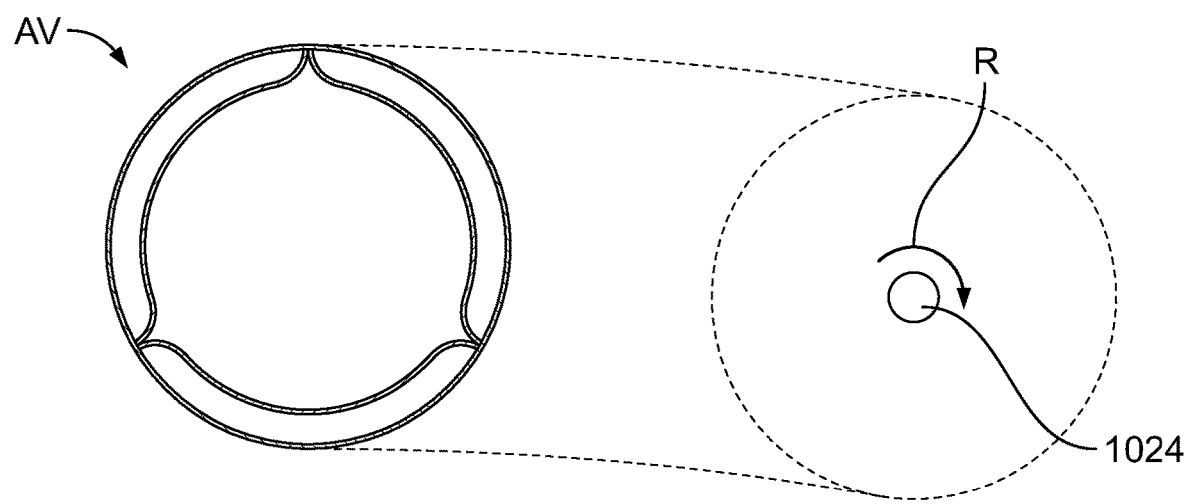
FIG. 11B is a highly schematic cross section of FIG. 11A taken through a plane traversing the aortic arch, illustrating the rotation of the delivery device.

In any of the embodiments described above that rely upon twisting of the delivery device 1010 (for example at or near the distal sheath 1024), instead of relying on twisting via applied torsion, components may be provided on the delivery device to allow for rotation without twisting. For example, FIG. 11A illustrates the delivery device 1010 including a joint J between the outer shaft 1022 and the distal sheath 1024. The joint J may take the form of a rotary bearing, such as a thrust bearing, that allows for rotation of the outer sheath 1024 in one rotational direction R or in both rotational directions about the longitudinal axis of the outer shaft 1024, as shown in FIG. 8B. However, it should be understood that other rotational joints J may be suitable other than thrust bearings. In some embodiments, it may be preferable to have friction about the joint J so that, while the distal sheath 1024 can rotate, the rotation is not totally free.

In a first exemplary method of performing commissure-to-commissure alignment in an aortic valve replacement procedure, prosthetic heart valve 200 is loaded into the compartment 1023 of delivery deice 1010 in a collapsed condition. Access to the patient's vasculature is obtained, for example, via the groin and a standard guidewire is delivered through the vasculature, around the aortic arch, through the native aortic valve AV, and into the left ventricle LV. Then, the distal end (e.g. distal tip 1014) of the delivery device 1010 is advanced over the proximal end of the guidewire so that the guidewire is positioned within a standard guidewire lumen of the delivery device 1010. The delivery device 1010 is advanced distally over the guidewire until the valve compartment 1023 (or the distal sheath 1024) is positioned at or adjacent the native aortic valve AV. Imaging (e.g. fluoroscopy, echocardiography, and/or other imaging modalities) may be performed to determine the relative rotational position between the commissures of the native aortic valve AV and the commissures of the prosthetic heart valve 200 within the compartment 1023. If it is determined that the prosthetic and native commissures are in the desired rotational alignment, the distal sheath 1024 may be retracted to allow the prosthetic heart valve 200 to expand (e.g. via self-expansion) into the annulus of the native aortic valve AV. If it is determined that the prosthetic and native commissures are not in the desired rotational alignment, the distal sheath 1024 (and/or the internal retainer system including retainers 1025) may be actively rotated to achieve the desired commissure-to-commissure alignment. For example, axial translation may be transformed into rotational movement of the distal sheath 2014 using the groove mechanisms of FIGS. 4A-B, the ball-screw-type mechanism of FIGS. 5A-B, the "click pen" type mechanism of FIGS. 6A-B, or the pull wire mechanism(s) of FIGS. 7A-B. The rotation of the distal sheath 1024 (and/or the internal retainer system) may be achieved by twisting of the component, or otherwise by rotation of the component via a joint such as a thrust bearing described in connection with FIGS. 11A-B. Then, once the desired rotational alignment has been achieved, the distal sheath 1024 may be withdrawn to allow the prosthetic heart valve 200 to expand into the annulus of the native aortic valve AV with the desired commissure-to-commissure alignment. Instead of using the standard guidewire mentioned directly above, one of the guidewires described in connection with FIGS. 9A-10B (or alternative embodiments described in connection with FIGS. 9A-10B) may be first inserted into the heart and then anchored at any desired location, including any of those described in connection with FIG. 8. If the particular guidewire that is used will only allow the delivery device 1010 to be positioned over the guidewire in one or a limited number of rotational positions, the known positioning of the guidewire may be used to determine the rotational position in which the prosthetic heart valve 200 is loaded into the compartment 1023, and the orientation in which the delivery device 1010 is positioned over the guidewire (if more than one position is possible). These pre-determined positions may be so that the distal sheath 1024, after being advanced over the guidewire to or adjacent the annulus of the native aortic valve AV, will already be in the desired rotational position (along with the prosthetic heart valve 200 housed therein) with respect to the native commissures. If a guidewire with a twisted annular section is employed, such as that described in connection with FIGS. 9A-C, any additional rotational change in the position of the prosthetic heart valve 200 may be achieved by advancing the delivery device along the twisted portion of the guidewire to twist (or rotate if a joint such as a thrust bearing is incorporated) the distal sheath 1024, until the desired rotational alignment is achieved. Then, the prosthetic heart valve 200 may be released from the distal sheath 1024 so that the prosthetic heart valve commissures align with the native commissures upon implantation.

Although various individual features for active commissure-to-commissure alignment are described herein, it should be understood that some of the features may be combinable into a single system. For example the use of any of the guidewires described herein may be combined with other active alignment mechanisms such as those described in connection with FIGS. 4A-7B.

Further, although much of the disclosure above is described in connection with a transfemoral approach to an aortic valve replacement, the invention is not so limited. For example, any of the embodiments described herein may be used (with or without modification depending on the application) in other delivery approaches to the native aortic valve AV, or via other delivery approaches for the replacement of the mitral valve, pulmonary valve, or the tricuspid valve.

According to one aspect of the disclosure, a delivery device for a collapsible prosthetic heart valve comprises:
 an inner shaft;
 an outer shaft;
 a distal sheath disposed distal to the outer shaft and about a portion of the inner shaft to form a compartment with the inner shaft, the compartment being sized to receive the prosthetic heart valve in a collapsed condition, the inner shaft and the distal sheath being movable relative to one another;
 a tube member; and
 an outer sleeve overlying the tube member,
 wherein the tube member is configured to rotate or twist upon axial movement of the outer sleeve with respect to the tube member, the rotation or twisting of the tube member configured to rotate the prosthetic heart valve when the prosthetic heart valve is received within the compartment in the collapsed condition; and/or
 the tube member includes at least one groove having an axial portion that transitions into a curved portion; and/or
 the curved portion of the groove is positioned distal to the axial portion of the groove; and/or
 the outer sleeve includes at least one protrusion extending radially inwardly from an inner surface of the outer sleeve, the at least one protrusion configured to be received within the at least one groove; and/or
 the tube member includes external threading; and/or
 the outer sleeve includes at least one protrusion extending inwardly from an inner surface thereof; and/or
 the at least one protrusion is configured to be received within spaces between adjacent peaks of the external threading; and/or
 at least one pull wire coupled to the outer sleeve, the at least one pull wire extending proximally toward a handle of the delivery device; and/or
 the tube member is a cam member that has angled surfaces that confront angled surfaces of a plunger, and the outer sleeve includes an internally projecting guide member adapted to translate within corresponding guide member recesses in the cam member and the plunger; and/or
 the plunger is configured to rotate the cam member in discrete rotational increments; and/or
 the tube member is configured to rotate about a joint upon axial movement of the outer sleeve with respect to the tube member; and/or
 the joint is a thrust bearing; and/or
 the tube member is configured to twist upon axial movement of the outer sleeve with respect to the tube member.

According to a further aspect of the disclosure, a delivery device for a collapsible prosthetic heart valve comprises:
 an inner shaft;
 an outer shaft;
 a distal sheath disposed distal to the outer shaft and about a portion of the inner shaft to form a compartment with the inner shaft, the compartment being sized to receive the prosthetic heart valve in a collapsed condition, the inner shaft and the distal sheath being movable relative to one another;
 a tube member; and
 a pull wire wrapped around the tube member, the pull wire having a first free end extending proximally toward a handle of the delivery device, wherein the tube member is configured to rotate or twist in a first rotational direction upon pulling of the first free end of the pull wire; and/or the pull wire includes a second end coupled to the tube member, the second end being positioned opposite the first free end; and/or the pull wire includes a second free end extending proximally toward the handle of the delivery device, the tube member being configured to rotate or twist in a second rotational direction upon pulling the second free end of the pull wire, the second rotational direction being opposite the first rotational direction.

According to still another aspect of the disclosure, a prosthetic heart valve delivery system comprises:
- a delivery device including:
  - an inner shaft;
  - an outer shaft;
  - a distal sheath disposed distal to the outer shaft and about a portion of the inner shaft to form a compartment with the inner shaft, the compartment being sized to receive the prosthetic heart valve in a collapsed condition, the inner shaft and the distal sheath being movable relative to one another; and
  - a guidewire having a proximal section, a distal anchoring section, and an annulus section between the proximal section and the distal anchoring section;
- wherein the annulus section of the guidewire has a non-circular cross-sectional shape that matches a non-circular cross-sectional shape of an interior guidewire lumen of the delivery device, the annulus section of the guidewire twisting along a length of the annulus section; and/or
- the distal anchoring section of the guidewire is formed as a coil.

According to still a further aspect of the disclosure, a prosthetic heart valve delivery system comprises:
- a delivery device including:
  - an inner shaft;
  - an outer shaft;
  - a distal sheath disposed distal to the outer shaft and about a portion of the inner shaft to form a compartment with the inner shaft, the compartment being sized to receive the prosthetic heart valve in a collapsed condition, the inner shaft and the distal sheath being movable relative to one another;
  - a first guidewire; and
  - a second guidewire;
- wherein the first and second guidewires have circular cross-sections, the delivery device defining a guidewire lumen configured to simultaneously receive therethrough the first and second guidewires, the delivery device having at most two different rotational orientations relative to the first and second guidewires when the first and second guidewires are received within the guidewire lumen; and/or
- the first guidewire and the second guidewire have a same diameter, and the guidewire lumen has a length that is at least twice as large as the diameter, and a width that is about equal to the diameter.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will be appreciated that the various dependent claims and the features set forth therein can be combined in different ways than presented in the initial claims. It will also be appreciated that the features described in connection with individual embodiments may be shared with others of the described embodiments.

The invention claimed is:

1. A prosthetic heart valve delivery system comprising:
a delivery device including:
an inner shaft;
an outer shaft;
a distal sheath disposed distal to the outer shaft and about a portion of the inner shaft to form a compartment with the inner shaft, the compartment being sized to receive the prosthetic heart valve in a collapsed condition, the inner shaft and the distal sheath being movable relative to one another; and
a guidewire having a proximal section, a distal anchoring section, and an annulus section between the proximal section and the distal anchoring section;
wherein the annulus section of the guidewire has a non-circular cross-sectional shape, the cross-sectional shape being taken along a plane that is transverse to a central longitudinal axis of the annulus section of the guidewire, that matches a non-circular cross-sectional shape of an interior guidewire lumen of the delivery device, the annulus section of the guidewire twisting along a length of the annulus section.

2. The prosthetic heart valve delivery system of claim 1, wherein the distal anchoring section of the guidewire is formed as a coil.

3. The prosthetic heart valve delivery system of claim 2, wherein the coil is sized and shaped to lodge into a left ventricular apex in order to anchor the distal anchoring section of the guidewire to a heart.

4. The prosthetic heart valve delivery system of claim 1, wherein the non-circular cross-sectional shape of the annulus section is elliptical.

5. The prosthetic heart valve delivery system of claim 4, wherein the elliptical shape has a major axis.

6. The prosthetic heart valve delivery system of claim 5, wherein an orientation of the major axis is in different rotational positions along the length of the annulus section.

7. The prosthetic heart valve delivery system of claim 4, wherein the non-circular cross-sectional shape of the interior guidewire lumen is elliptical.

8. The prosthetic heart valve delivery system of claim 7, wherein the delivery device is not capable of freely rotating about the guidewire.

* * * * *